(12) United States Patent
Bowles

(10) Patent No.: US 9,357,783 B2
(45) Date of Patent: *Jun. 7, 2016

(54) METHODS AND COMPOSITIONS FOR CONTROLLING ECTOPARASITES

(75) Inventor: Vernon Morrison Bowles, Glen Iris (AU)

(73) Assignee: HatchTech Pty Ltd., Camberwell, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/540,302

(22) Filed: Jul. 2, 2012

(65) Prior Publication Data

US 2013/0005765 A1    Jan. 3, 2013

Related U.S. Application Data

(63) Continuation of application No. 12/902,841, filed on Oct. 12, 2010, now Pat. No. 8,212,038, which is a continuation of application No. 11/332,856, filed on Jan. 13, 2006, now Pat. No. 7,812,163, which is a continuation-in-part of application No. PCT/AU2004/000955, filed on Jul. 16, 2004.

(60) Provisional application No. 60/645,824, filed on Jan. 20, 2005, provisional application No. 60/487,717, filed on Jul. 16, 2003.

(30) Foreign Application Priority Data

Jul. 16, 2003 (AU) ................................ 2003903686

(51) Int. Cl.

| A01N 43/42 | (2006.01) |
| A01N 57/32 | (2006.01) |
| A01N 37/44 | (2006.01) |
| A01N 37/46 | (2006.01) |
| A01N 43/36 | (2006.01) |
| A01N 43/40 | (2006.01) |
| A01N 43/90 | (2006.01) |

(52) U.S. Cl.
CPC ................ *A01N 57/32* (2013.01); *A01N 37/44* (2013.01); *A01N 37/46* (2013.01); *A01N 43/36* (2013.01); *A01N 43/40* (2013.01); *A01N 43/42* (2013.01); *A01N 43/90* (2013.01)

(58) Field of Classification Search
CPC ........ A01N 43/40; A01N 43/42; A01N 43/90
See application file for complete search history.

(56) References Cited

U.S. PATENT DOCUMENTS

| 4,177,349 | A | * | 12/1979 | McGill .......................... 546/255 |
| 4,690,818 | A | * | 9/1987 | Puchalski et al. .......... 424/70.14 |
| 5,100,436 | A | * | 3/1992 | Wenke .............................. 8/405 |
| 5,112,515 | A | * | 5/1992 | Buxton et al. ................. 514/531 |
| 5,200,427 | A | * | 4/1993 | Rebeiz et al. .................. 514/561 |
| 5,608,059 | A | * | 3/1997 | Wear et al. .................... 540/465 |
| 7,812,163 | B2 | * | 10/2010 | Bowles ............................ 546/2 |
| 8,212,038 | B2 | * | 7/2012 | Bowles ............................ 546/2 |
| 2002/0032339 | A1 | * | 3/2002 | Marcuccio et al. ........... 549/456 |

OTHER PUBLICATIONS

Case, The Synthesis of Certain Substituted 2,2'-Biyridyls, Journal of American Chemical Society, vol. 68, pp. 2574-2577.*
Final Report on the Safety Assessment of EDTA, Calcium Disodium EDTA, Diammonium EDTA, Dipotassium EDTA, Disodium EDTA, Tea-EDTA, Tetrasodium EDTA, Tripotassium EDTA, Trisodium EDTA, HEDTA, and Trisodium HEDTA, International Journal of Toxicology, 21, (Suppl. 2):95-142, 2002.

* cited by examiner

*Primary Examiner* — Ali Soroush
(74) *Attorney, Agent, or Firm* — McAndrews, Held & Malloy, Ltd.

(57) ABSTRACT

A method for inhibiting hatching of an ectoparasite egg, the method comprising exposing the ectoparasite egg to at least one metal chelating agent and/or metalloprotease inhibitor, wherein the metal chelating agent is a compound comprising at least two heteroatoms able to simultaneously coordinate with a metal ion, at least one of the two heteroatoms being selected from nitrogen, sulfur, oxygen and phosphorus, wherein the compound comprises at least one carbocyclic ring substituted with at least one heteroatom and/or with a substituent containing at least one heteroatom, or the compound comprises at least one heterocyclic ring containing at least one heteroatom, wherein said heterocyclic ring is optionally substituted with at least one heteroatom and/or with a substituent containing at least one heteroatom is provided. Methods of treating ectoparasite infestations and compositions for use in such methods are also provided.

16 Claims, 4 Drawing Sheets

METHODS AND COMPOSITIONS FOR CONTROLLING ECTOPARASITES

This application is a continuation of and claims the benefit of U.S. patent application Ser. No. 12/902,841 filed Oct. 12, 2010, now U.S. Pat. No. 8,212,038, issued Jul. 3, 2012, which is a continuation of U.S. patent application Ser. No. 11/332, 856 filed Jan. 13, 2006, now U.S. Pat. No. 7,812,163, issued Oct. 12, 2010, which is a continuation in part of International Patent Applications PCT/AU04/000955, filed Jul. 16, 2004, which claims the benefit of U.S. Provisional Patent Application Ser. No. 60/487,717, filed Jul. 16, 2003. This application and U.S. patent application Ser. No. 11/332,856 also claim the benefit of U.S. Provisional Patent Application Ser. No. 60/645,824, filed Jan. 20, 2005. This application also claims the benefit of Australian Patent Application No. 2003903686, filed Jul. 16, 2003. The content of each of the preceding are hereby incorporated by reference in their entirety.

BACKGROUND OF THE INVENTION

1. Field of the Invention

The present invention relates to methods and compositions for controlling ectoparasites. In particular, the invention relates to methods and compositions for inhibiting hatching of an ectoparasite egg. The invention also provides methods and compositions for preventing or treating ectoparasite infestation. The invention also relates to methods for identifying compounds that can inhibit ectoparasite egg hatching.

2. Description of the Related Art

Ectoparasites including some insects cause significant pest problems in a wide variety of animals and plants. In particular, ectoparasites typically can annoy, bite, and cause infections to humans and domesticated animals. Of particular concern is the presence and effect of such parasites on humans, household pets or companion animals, such as dogs and cats, and other domesticated animals, such as sheep, cattle and horses. Of equal concern is that ectoparasites can also cause significant damage to plants. Larvae can eat leaves, flowers and fruit of commercially important plants causing millions of dollars of damage every year.

Various compositions and application techniques are known for controlling or eliminating plant pests, such as caterpillars, moths and butterflies, and biting or blood-sucking pests (ectoparasites), such as fleas, ticks, flies, lice and mites. Over the years a host of aerosols and space sprays, liquids, soaps, shampoos, wettable powders, granules, baits, and dusts, have been proposed for the control of such ectoparasites.

Conventional control measures for ectoparasites have relied on the use of chemical insecticides, for example chlorinated hydrocarbons (DDT, endosulfan etc), and synthetic and natural pyrethroids (pyrethrin, permethrin, cypermethrin, deltamethrin). Problems associated with the use of chemical pesticides include the development of resistance by target ectoparasites, the persistence of the chemicals in the environment and in plant and animal tissues, and the harmful effects on host and non-target organisms.

Other types of ectoparasiticides include insecticides, such as insect growth regulators (IGRs) that are known to interfere with chitin synthesis and insecticidal bacterial toxins (e.g., *Bacillus thuringiensis* (Bt) toxins). More useful groups of insecticides are those having high insecticidal activity and low environmental persistence, such as organophosphates and natural pyrethrins. However, a significant problem associated with these insecticides is the development of resistance by target insects.

For example, insecticidal agents used to treat lice are described in EP 0191236 and U.S. Pat. No. 5,288,483. A significant disadvantage of using these agents is that lice can become resistant. The need for further treatment increases the exposure to these harsh agents and increases the cost. Additionally, clinicians and parents are reluctant to treat children with agents that can also prove toxic to human beings. Moreover, many of these compounds have unpleasant odors or other undesirable properties, causing noncompliance by the patient, leading to re-infestation of the individual, and spreading of the infestation to others. In addition, the harshness of these agents makes them unsuitable for use as prophylactics.

In the case of head lice infestation, home remedies such as application of corn oil, olive oil, eucalyptus oil, neem oil, coconut oil, mayonnaise, or petroleum jelly for a period of time sufficient to kill the lice (e.g., overnight) are not practical or completely effective. A further disadvantage of methods to treat head lice is the requirement of removing the eggs and nits from the hair in a separate treatment step. The removal of eggs and nits has typically been done by hand using special fine-tooth combs. Use of combing alone to treat eggs, nits and head lice has disadvantages that the eggs are difficult to remove and similarly lice can hold onto the hair shafts using their claws or escape by crawling away from the area being combed. This labor intensive method requires daily combing, is painful, and is unpleasant since the lice are active, visible and crawling.

There is a significant need for improved control of lice throughout the world. In particular, there are well-documented failures of products aimed at treating lice. The development of resistance of lice to many of the currently used chemicals including permethrin, pyrethrin and malathion is considered a major factor in treatment failures. In addition, inappropriate formulations containing suboptimal actives are also believed to be in part responsible for resistance development. More recently there has been significant growth in the market for herbal products for treating head lice however there is very little published evidence from properly conducted trials to enable an effective assessment of these products to be made. Furthermore while a number of products claim to possess ovicidal activity the evidence for this in the field is far from convincing hence it is common for products to recommend that following an initial treatment a second treatment should be given between 7-14 days later to kill newly emerged nymphs.

Development of resistance is also a problem with chemical control of ectoparasites that infest plants. Although biological and chemical control methods have also been used to control plant ectoparasites by controlling or killing larvae after they emerge from their eggs, such control reduces rather than eliminates the damage to plants caused by ectoparasites.

Recently attention has focused on insect proteases that may provide a possible means of ectoparasite control. Proteases perform a variety of functions in the organism including the regulation and breakdown of proteins and peptides, and thus assist with digestion. They are also involved in tissue reorganization during embryo development, moulting and pupation. Proteases are a widely variable group of enzymes and include digestive proteases that vary considerably both in number and in catalytic properties within and between species. For example, trypsin-like serine proteases have been recognized to be involved in the key growth regulatory area of moulting (Samuels R. I. and Paterson C. J., *Comparative Biochemistry and Physiology*, 1995, 1108: 661-669).

Protease inhibitors have been suggested to be a useful alternative to the chemical control methods, particularly where the ectoparasites have become resistant to chemical pesticides. In particular, serine and cysteine protease inhibitors have been shown to reduce the larval growth and/or survival of various insects (Dymock et. al., *New Zealand Journal of Zoology*, 1992, 19: 123-131). Growth inhibition has been achieved with inhibitors of principal digestive enzymes of the gut and have been targeted at ectoparasite larvae or mature parasites. However, little is known about other types of activity and function of various classes of protease inhibitors. A common problem of existing ectoparasiticides is that they do not effect the ectoparasite eggs and therefore application of the parasiticides to hosts often require repeated treatment or prolonged exposure to the parasiticide for it to be effective. This is not only inconvenient but also increases risks to the environment and to the host.

Accordingly, there remains a need for providing alternative methods and compositions that are effective in inhibiting ectoparasite egg hatching to provide efficient control of ectoparasites.

BRIEF SUMMARY OF THE INVENTION

In an aspect of the invention there is provided a method for inhibiting hatching of an ectoparasite egg comprising exposing the ectoparasite egg to at least one metal chelating agent, wherein the metal chelating agent is a compound comprising at least two heteroatoms able to simultaneously coordinate with a metal ion, at least one of the two heteroatoms being selected from nitrogen, sulfur, oxygen and phosphorus, wherein the compound comprises at least one carbocyclic ring substituted with at least one heteroatom and/or with a substituent containing at least one heteroatom, or the compound comprises at least one heterocyclic ring containing at least one heteroatom, wherein said heterocyclic ring is optionally substituted with at least one heteroatom and/or with a substituent containing at least one heteroatom. In one embodiment, the ectoparasite egg is one infesting a plant host. In another embodiment, the ectoparasite egg is one infesting a domesticated animal. In yet another embodiment, the ectoparasite egg is one infesting a human.

The present applicants have identified metal chelating agents and metalloprotease inhibitors as effective agents for inhibiting ectoparasite egg hatching. The use of metal chelating agents or metalloprotease inhibitors for inhibiting ectoparasite egg hatching has the advantage of preventing breeding cycles of ectoparasites thereby controlling ectoparasite infestation.

In another aspect there is provided a method of treating or preventing ectoparasite infestation in a host comprising applying an effective amount of at least one chelating agent, wherein the metal chelating agent is a compound comprising at least two heteroatoms able to simultaneously coordinate with a metal ion, at least one of the two heteroatoms being selected from nitrogen, sulfur, oxygen and phosphorus, wherein the compound comprises at least one carbocyclic ring substituted with at least one heteroatom and/or with a substituent containing at least one heteroatom, or the compound comprises at least one heterocyclic ring containing at least one heteroatom, wherein said heterocyclic ring is optionally substituted with at least one heteroatom and/or with a substituent containing at least one heteroatom. In one embodiment, the host is a plant. In another embodiment, the host is a domesticated animal. In yet another embodiment, the host is a human.

In yet a further aspect of the invention there is provided a method of treating or preventing ectoparasite infestation in a host comprising applying an effective amount of at least one compound of formula (Ia):

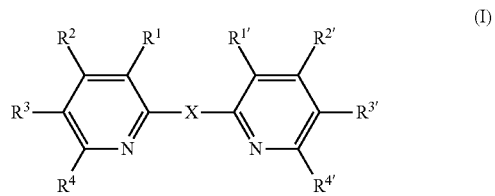

wherein X is selected from a covalent bond, —C(R$^5$)$_2$—, —Z— or —C(R$^5$)$_2$—Z—C(R$^5$)$_2$—;

R$^1$ and R$^{1'}$ are independently selected from hydrogen, C$_{1-6}$alkyl, C$_{2-6}$alkenyl, C$_{2-6}$alkynyl, hydroxy, C$_{1-6}$alkoxy, thiol, C$_{1-6}$alkylthio, halogen, C(R$^6$)$_3$, CO$_2$H, CO$_2$C$_{1-6}$alkyl, SO$_3$H, SO$_3$C$_{1-6}$alkyl, NH$_2$, NHC$_{1-6}$alkyl or N(C$_{1-6}$alkyl)$_2$;

R$^2$, R$^{2'}$, R$^3$, R$^{3'}$, R$^4$ and R$^{4'}$ are independently selected from hydrogen, C$_{1-6}$alkyl, C$_{2-6}$alkenyl, C$_{2-6}$alkynyl, hydroxy, C$_{1-6}$alkoxy, thiol, C$_{1-6}$alkylthiol, halogen, CN, C(R$^6$)$_3$, CO$_2$H, CO$_2$C$_{1-6}$alkyl, SO$_3$H, SO$_3$C$_{1-6}$alkyl, NH$_2$, NHC$_{1-6}$alkyl or N(C$_{1-6}$alkyl)$_2$, —CH$_2$CHNH(CO$_2$H), NH(C$_{1-6}$alkylene)N(C$_{1-6}$alkyl)$_2$ or a 5 or 6 membered carbocyclic or heterocyclic ring; or R$^2$ and R$^3$ or R$^3$ and R$^4$ and/or R$^{2'}$ and R$^{3'}$ or R$^{3'}$ and R$^{4'}$ taken together with the carbon atoms to which they are attached form a 5 or 6 membered carbocyclic or heterocyclic ring;

each R$^5$ is independently selected from hydrogen, C$_{1-6}$alkyl, C$_{2-6}$alkenyl, C$_{2-6}$alkynyl, hydroxy, C$_{1-6}$alkoxy, thiol, C$_{1-6}$alkylthiol, CO$_2$H, CO$_2$C$_{1-6}$alkyl, SO$_3$H, SO$_3$C$_{1-6}$alkyl, NH$_2$, NHC$_{1-6}$alkyl or N(C$_{1-6}$alkyl)$_2$;

each R$^6$ is independently selected from hydrogen and halogen; and

Z is selected from a covalent bond, —NH—, —O—, —S—, —C(O)— and —C(S)—;

or a pharmaceutically, veterinary or agriculturally acceptable salt thereof.

In a further aspect of the invention there is provided a composition for inhibiting hatching of an ectoparasite egg comprising an effective amount of at least one metal chelating agent, wherein the metal chelating agent is a compound comprising at least two heteroatoms able to simultaneously coordinate with a metal ion, at least one of the two heteroatoms being selected from nitrogen, sulfur, oxygen and phosphorus, wherein the compound comprises at least one carbocyclic ring substituted with at least one heteroatom and/or with a substituent containing at least one heteroatom, or the compound comprises at least one heterocyclic ring containing at least one heteroatom, wherein said heterocyclic ring is optionally substituted with at least one heteroatom and/or with a substituent containing at least one heteroatom and a suitable diluent, excipient or carrier. In one embodiment, the ectoparasite egg is one infesting a plant host. In another embodiment, the ectoparasite egg is one infesting a domesticated animal. In yet another embodiment, the ectoparasite egg is one infesting a human.

DETAILED DESCRIPTION OF THE PREFERRED EMBODIMENTS

Figure 1:
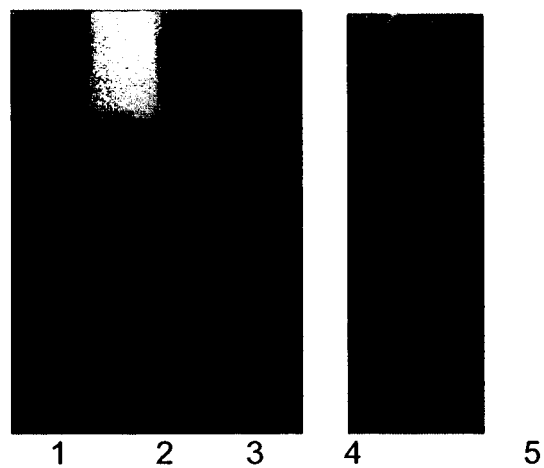
FIG. 1: shows a gelatine substrate SDS-PAGE analysis of protease activity of washings obtained from various samples of hair and lice eggs following staining of the gel with Coomassie blue and destaining. Lane 1 shows protease activity detected in the washings obtained from unhatched lice eggs within 12 hours of hatching. Protease activity was in the higher molecular weight region of the SDS gel. Lane 2 shows protease activity detected in the washings collected from human hair from which that gravid female lice had recently been removed, and indicates the presence of a number of highly active and stable proteases likely to be of maternal origin. Lane 3 contained the washings collected from a similar hair sample as described above that was washed with a 1% solution of sodium hypochlorite for 1 minute followed by a number of water washes in an attempt to remove these contaminating proteases. This treatment was able to remove the maternal proteases resulting in no protease species being detected in the hair only sample. Lane 4 shows protease activity detected in the washings from eggs within 12 hours of egg hatching treated with sodium hypochlorite (as described above). This treatment removed the protease activity that was observed in the unwashed sample (compare to lane 1). Lane 5 shows the presence of one or two high molecular weight protease species in egg washings from lice eggs that had been pretreated with sodium hypochlorite and allowed to hatch. The sample in lane 5 was collected 0-2 hours post egg hatch. These proteases were specifically associated with the lice eggs at the time of egg hatching and were termed egg shell washings (ESW).

As used herein, the term "metal chelating agent" refers to a compound comprising at least two heteroatoms able to simultaneously coordinate with a metal ion, at least one of the two heteroatoms being selected from nitrogen, sulfur, oxygen or phosphorus, wherein the compound comprises at least one carbocyclic ring substituted with at least one heteroatom and/or a substituent containing at least one heteroatom, or the compound comprises at least one heterocyclic ring containing at least one heteroatom, and wherein said heterocyclic ring is optionally substituted with at least one heteroatom and/or a substituent containing at least one heteroatom. Preferably the metal chelating agent contains an aryl or heteroaryl ring. More preferably, the metal chelating agent comprises at least one nitrogen heteroatom. Preferably the metal chelating agent is non-intercalating.

As used herein, the term "metalloprotease inhibitor" refers to a molecule, compound, protein or agent that inhibits the activity of a metalloprotease associated with ectoparasite egg hatching. The inhibition may be inhibition of the expression of the metalloprotease or inhibition of the enzymatic activity of the metalloprotease. Preferred metalloprotease inhibitors are metal chelating agents.

Preferred metal chelating agents are selected from biaryl compounds, peptides and amino acid derivatives, tetracyclic antibiotics and thioureas. Preferred biaryl compounds include bipyridyl compounds and 1,10-phenanthroline compounds.

In one embodiment the metal chelating agent is a compound of formula (I):

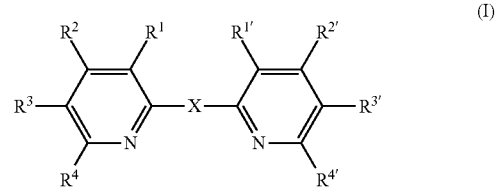

wherein X is selected from a covalent bond, —C($R^5$)$_2$—, —Z— or —C($R^5$)$_2$—Z—C($R^5$)$_2$—;

$R^1$ and $R^{1'}$ are independently selected from hydrogen, $C_{1-6}$alkyl, $C_{2-6}$alkenyl, $C_{2-6}$alkynyl, hydroxy, $C_{1-6}$alkoxy, thiol, $C_{1-6}$alkylthio, halogen, C($R^6$)$_3$, $CO_2H$, $CO_2C_{1-6}$alkyl, $SO_3H$, $SO_3C_{1-6}$alkyl, $NH_2$, $NHC_{1-6}$alkyl or $N(C_{1-6}$alkyl)$_2$, or $R^1$ and $R^{1'}$ taken together are —C($R^5$)$_2$—, —C($R^5$)$_2$—C($R^5$)$_2$—, —$CR^5$=$CR^5$—, C(O), C(S) or NH;

$R^2$, $R^{2'}$, $R^3$, $R^{3'}$, $R^4$ and $R^{4'}$ are independently selected from hydrogen, $C_{1-6}$alkyl, $C_{2-6}$alkenyl, $C_{2-6}$alkynyl, hydroxy, $C_{1-6}$alkoxy, thiol, $C_{1-6}$alkylthiol, halogen, CN, C($R^6$)$_3$, $CO_2H$, $CO_2C_{1-6}$alkyl, $SO_3H$, $SO_3C_{1-6}$alkyl, $NH_2$, $NHC_{1-6}$alkyl or $N(C_{1-6}$alkyl)$_2$, —$CH_2$CHNH($CO_2H$), $NH(C_{1-6}$alkylene)$N(C_{1-6}$alkyl)$_2$ or a 5 or 6 membered carbocyclic or heterocyclic ring; or $R^2$ and $R^3$ or $R^3$ and $R^4$ and/or $R^{2'}$ and $R^{3'}$ or $R^{3'}$ and $R^{4'}$ taken together with the carbon atoms to which they are attached form a 5 or 6 membered carbocyclic or heterocyclic ring;

each $R^5$ is independently selected from hydrogen, $C_{1-6}$alkyl, $C_{2-6}$alkenyl, $C_{2-6}$alkynyl, hydroxy, $C_{1-6}$alkoxy, thiol, $C_{1-6}$alkylthiol, $CO_2H$, $CO_2C_{1-6}$alkyl, $SO_3H$, $SO_3C_{1-6}$alkyl, $NH_2$, $NHC_{1-6}$alkyl or $N(C_{1-6}$alkyl)$_2$;

each $R^6$ is independently selected from hydrogen and halogen; and

Z is selected from a covalent bond, —NH—, —O—, —S—, —C(O)— and —C(S)—;

or a pharmaceutically, veterinary or agriculturally acceptable salt thereof.

Preferred compounds of formula (I) have at least one of the following features:

$R^1$ and $R^{1'}$ are independently selected from $C_{1-6}$alkyl, $C_{2-6}$alkenyl, $C_{2-6}$alkynyl, hydroxy, $C_{1-6}$alkoxy, thiol, $C_{1-6}$alkylthio, $CO_2H$, $CO_2C_{1-6}$alkyl, $SO_3H$, $SO_3C_{1-6}$alkyl, $NH_2$, $NHC_{1-6}$alkyl or $N(C_{1-6}$alkyl)$_2$, more preferably hydrogen or $C_1$-$C_3$alkyl, even more preferably hydrogen or methyl;

$R^2$ and $R^{2'}$ are independently hydrogen or $C_{1-3}$alkyl, more preferably hydrogen;

$R^3$, $R^{3'}$, $R^4$ and $R^{4'}$ are independently selected from hydrogen, $C_{1-6}$alkyl, $C_{2-6}$alkenyl, $C_{2-6}$alkynyl, $C_{1-6}$alkoxy, $C_{1-6}$alkylthiol or $CO_2C_{1-6}$alkyl, preferably hydrogen or $C_{1-3}$alkyl, more preferably hydrogen or methyl; or $R^3$ and $R^4$ and/or $R^{3'}$ and $R^{4'}$ taken together with the carbon atoms to which they are attached form a 5 or 6 membered carbocyclic or heterocyclic ring, preferably an aromatic ring;

each $R^5$ is independently selected from hydrogen, $C_{1-6}$alkyl, $C_{2-6}$alkenyl, $C_{2-6}$alkynyl, $C_{1-6}$alkoxy, $C_{1-6}$alkylthiol or $CO_2C_{1-6}$alkyl, preferably hydrogen or $C_{1-3}$alkyl, more preferably hydrogen or methyl;

each $R^6$ is independently hydrogen or fluorine, especially where each $R^6$ is fluorine;

X is a covalent bond, —$CH_2$—Z—$CH_2$— or Z, preferably a covalent bond; and

Z is —NH—, —O— or —S—, preferably —NH—.

Preferred compounds of formula (I) are biaryl compounds of formula (Ia):

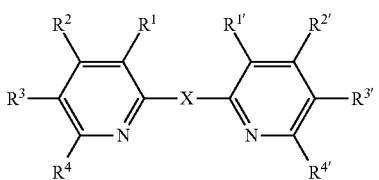

(Ia)

wherein X is selected from a covalent bond, —$C(R^5)_2$—, —Z— or —$C(R^5)_2$—Z—$C(R^5)_2$—;

$R^1$ and $R^{1'}$ are independently selected from hydrogen, $C_{1-6}$alkyl, $C_{2-6}$alkenyl, $C_{2-6}$alkynyl, hydroxy, $C_{1-6}$alkoxy, thiol, $C_{1-6}$alkylthio, halogen, $C(R^6)_3$, $CO_2H$, $CO_2C_{1-6}$alkyl, $SO_3H$, $SO_3C_{1-6}$alkyl, $NH_2$, $NHC_{1-6}$alkyl or $N(C_{1-6}$alkyl$)_2$;

$R^2$, $R^{2'}$, $R^3$, $R^{3'}$, $R^4$ and $R^{4'}$ are independently selected from hydrogen, $C_{1-6}$alkyl, $C_{2-6}$alkenyl, $C_{2-6}$alkynyl, hydroxy, $C_{1-6}$alkoxy, thiol, $C_{1-6}$alkylthiol, halogen, CN, $C(R^6)_3$, $CO_2H$, $CO_2C_{1-6}$alkyl, $SO_3H$, $SO_3C_{1-6}$alkyl, $NH_2$, $NHC_{1-6}$alkyl or $N(C_{1-6}$alkyl$)_2$, —$CH_2CHNH(CO_2H)$, $NH(C_{1-6}$alkylene$)N(C_{1-6}$alkyl$)_2$ or a 5 or 6 membered carbocyclic or heterocyclic ring; or $R^2$ and $R^3$ or $R^3$ and $R^4$ and/or $R^{2'}$ and $R^{3'}$ or $R^{3'}$ and $R^{4'}$ taken together with the carbon atoms to which they are attached form a 5 or 6 membered carbocyclic or heterocyclic ring;

each $R^5$ is independently selected from hydrogen, $C_{1-6}$alkyl, $C_{2-6}$alkenyl, $C_{2-6}$alkynyl, hydroxy, $C_{1-6}$alkoxy, thiol, $C_{1-6}$alkylthiol, $CO_2H$, $CO_2C_{1-6}$alkyl, $SO_3H$, $SO_3C_{1-6}$alkyl, $NH_2$, $NHC_{1-6}$alkyl or $N(C_{1-6}$alkyl$)_2$;

each $R^6$ is independently selected from hydrogen and halogen; and

Z is selected from a covalent bond, —NH—, —O—, —S—, —C(O)— and —C(S)—;

or a pharmaceutically, veterinary or agriculturally acceptable salt thereof.

Preferred compounds of formula (I) include
2,2'-dipyridyl,
6,6'-dimethyl 2,2'-dipyridyl,
5,5'-dimethyl 2,2'-dipyridyl,
4,4'-dimethyl 2,2'-dipyridyl, and
2-(2-pyridinyl)quinolone,
or a pharmaceutically, veterinary or agriculturally acceptable salt thereof.

In another embodiment, the metal chelating agent is a compound of formula (II):

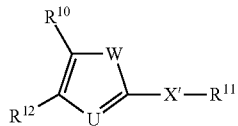

(II)

wherein X' is selected from a covalent bond, —$C(R^{13})_2$—, Z' or $C(R^{13})_2$—Z'—$C(R^{13})_2$—;

U is selected from N or $C(R^{13})$;

W is selected from —NH—, —S— or —O—;

Z' is selected from a covalent bond, —NH—, —O—, —S—, —C(O)—, or —C(S)—;

$R^{10}$ is selected from hydrogen, $C_{1-6}$alkyl, $C_{2-6}$alkenyl, $C_{2-6}$alkynyl, hydroxy, $C_{1-6}$alkoxy, thiol, $C_{1-6}$alkylthiol, $CO_2H$, $CO_2C_{1-6}$alkyl, $SO_3H$, $SO_3C_{1-6}$alkyl, $NH_2$, $NH(C_{1-6}$alkyl$)$, $N(C_{1-6}$alkyl$)_2$, or —$(CH_2)_nR^{14}$;

$R^{11}$ is selected from $(CH_2)_m$aryl or $(CH_2)_m$heteroaryl wherein each aryl or heteroaryl is optionally substituted with one or more $C_{1-6}$alkyl, $C_{2-6}$alkenyl, $C_{2-6}$alkynyl, hydroxy, $C_{1-6}$alkoxy, thiol, $C_{1-6}$alkylthiol, $CO_2H$, $CO_2C_{1-6}$alkyl, $SO_3H$, $SO_3C_{1-6}$alkyl, $NH_2$, $NH(C_{1-6}$alkyl$)$, $N(C_{1-6}$alkyl$)_2$, or halo;

each $R^{12}$ is independently selected from hydrogen, $C_{1-6}$alkyl, $C_{2-6}$alkenyl, $C_{2-6}$alkynyl, hydroxy, $C_{1-6}$alkoxy, thiol, $C_{1-6}$alkylthiol, $CO_2H$, $CO_2C_{1-6}$alkyl, $SO_3H$, $SO_3C_{1-6}$alkyl, $NH_2$, $NH(C_{1-6}$alkyl$)$, $N(C_{1-6}$alkyl$)_2$, or —$(CH_2)_nR^{14}$; or $R^{10}$ and $R^{12}$ together with the carbon atoms to which they are attached form a 5 or 6 membered carbocyclic or heterocyclic ring;

each $R^{13}$ is independently selected from hydrogen, $C_{1-6}$alkyl, $C_{2-6}$alkenyl, $C_{2-6}$alkynyl, hydroxy, $C_{1-6}$alkoxy, thiol, $C_{1-6}$alkylthiol, $CO_2H$, $CO_2C_{1-6}$alkyl, $SO_3H$, $SO_3C_{1-6}$alkyl, $NH_2$, $NH(C_{1-6}$alkyl$)$, $N(C_{1-6}$alkyl$)_2$, or —$(CH_2)_nR^{14}$;

$R^{14}$ is selected from $NH_2$, OH, SH or $CO_2H$;

m is 0 or an integer from 1 to 4; and n is an integer from 1 to 4;

or a pharmaceutically, veterinary or agriculturally acceptable salt thereof.

Preferred compounds of formula (II) have at least one of the following features:

X is a covalent bond or —$CH_2$—Z—$CH_2$—;

U is N;

W is NH or S;

Z' is NH;

$R^{10}$ is hydrogen, $C_{1-6}$alkyl, $C_{2-6}$alkenyl, $C_{2-6}$alkynyl, or $(CH_2)_nR^{14}$, preferably hydrogen, $C_{1-3}$alkyl or $(CH_2)_nR^{14}$;

$R^{11}$ is phenyl, phenyl substituted with $C_{1-3}$alkyl or halo, thiophene, pyridine, pyridinylmethyl, imidazole or imidazole substituted with one or two $C_{1-3}$alkyl;

$R^{12}$ is hydrogen, $C_{1-6}$alkyl, $C_{2-6}$alkenyl, $C_{2-6}$alkynyl, or $(CH_2)_nR^{14}$, preferably hydrogen, $C_{1-3}$alkyl or $(CH_2)_nR^{14}$; or $R^{10}$ and $R^{12}$ together with the carbon atoms to which they are attached form a fused phenyl ring;

$R^{13}$ is hydrogen or $C_{1-3}$alkyl, preferably hydrogen or methyl;

$R^{14}$ is $NH_2$ or $CO_2H$—, m is 0 or 1; and n is 1 or 2.

In another embodiment the metal chelating agent is selected from a compound of formula (III):

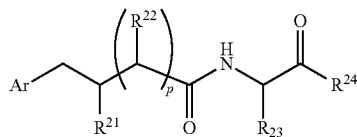
(III)

wherein Ar is phenyl, naphthyl or indolyl optionally substituted with one or more $C_{1-6}$alkyl, $C_{2-6}$alkenyl, $C_{2-6}$alkynyl, hydroxy, $C_{1-6}$alkoxy, thiol, $C_{1-6}$alkylthiol, $CO_2H$, $CO_2C_{1-6}$alkyl, $SO_3H$, $SO_3C_{1-6}$alkyl, $NH_2$, $NH(C_{1-6}$alkyl), $N(C_{1-6}$alkyl$)_2$;

$R^{21}$ is selected from $NH_2$, $NHR^{25}$ or —$CH_2SR^{25}$;

$R^{22}$ is selected from hydrogen, hydroxy or $C_{1-6}$alkoxy;

$R^{23}$ is selected from hydrogen, $C_{1-6}$alkyl, $C_{2-6}$alkenyl or $C_{2-6}$alkynyl;

$R^{24}$ is selected from OH, $OR^{26}$, $NH_2$, $NHC_{1-6}$alkyl or $N(C_{1-6}$alkyl$)_2$;

$R^{25}$ is selected from hydrogen, $C(O)C_{1-6}$alkyl wherein the alkyl is optionally substituted with —SH or —OH;

$R^{26}$ is selected from $C_{1-6}$alkyl, $C_{2-6}$alkenyl, $C_{2-6}$alkynyl or benzyl; and p is 0 or 1, or a pharmaceutically, veterinary or agriculturally acceptable salt thereof.

Preferred compounds of formula (III) have at least one of the following features:

Ar is phenyl or naphthyl;

$R^{21}$ is $NH_2$, —$NHC(O)C_{1-6}$alkyl optionally substituted with SH, —$CH_2SC(O)C_{1-6}$alkyl or $CH_2SH$;

$R^{22}$ is hydrogen or hydroxy;

$R^{23}$ is hydrogen or $C_{1-3}$alkyl, preferably hydrogen or methyl;

$R^{24}$ is OH, $NH_2$ or Obenzyl; and p is 0 or 1.

Preferred compounds of formula III include Bestatin and Thiorophan or a pharmaceutically, veterinary or agriculturally acceptable salt thereof.

In yet another embodiment, the metal chelating agent is a compound of formula (IV):

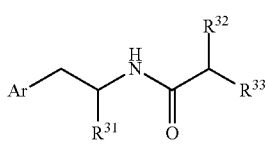
(IV)

wherein Ar is phenyl, naphthyl or indolyl optionally substituted with one or more $C_{1-6}$alkyl, $C_{2-6}$alkenyl, $C_{2-6}$alkynyl, hydroxy, $C_{1-6}$alkoxy, thiol, $C_{1-6}$alkylthiol, $CO_2H$, $CO_2C_{1-6}$alkyl, $SO_3H$, $SO_3C_{1-6}$alkyl, $NH_2$, $NH(C_{1-6}$alkyl), $N(C_{1-6}$alkyl$)_2$;

$R^{31}$ is selected from $CO_2H$, $CO_2C_{1-6}$alkyl, $CO_2C_{2-6}$alkenyl, $CO_2C_{2-6}$alkynyl, $CONH_2$, $CONH(C_{1-6}$alkyl) or $CON(C_{1-6}$alkyl$)_2$;

$R^{32}$ is selected from hydrogen, $C_{1-6}$alkyl, $C_{2-6}$alkenyl, $C_{2-6}$alkynyl, hydroxy, $C_{1-6}$alkoxy, thiol, $C_{1-6}$alkylthiol, $CO_2H$, $CO_2C_{1-6}$alkyl, $SO_3H$, $SO_3C_{1-6}$alkyl, $NH_2$, $NH(C_{1-6}$alkyl), $N(C_{1-6}$alkyl$)_2$, $CH_2CH_2CO_2H$, $CH_2CH_2CONH_2$, $CH_2CH_2OH$, $CH_2CH_2SH$; and $R^{33}$ is selected from $C_{1-6}$alkyl, $C_{2-6}$alkenyl, $C_{2-6}$alkynyl, hydroxy, $C_{1-6}$alkoxy, thiol, $C_{1-6}$alkylthiol, $CO_2H$, $CO_2C_{1-6}$alkyl, $SO_3H$, $SO_3C_{1-6}$alkyl, $NH_2$, $NH(C_{1-6}$alkyl), $N(C_{1-6}$alkyl$)_2$, $CH_2CO_2H$, $CH_2CO_2C_{1-6}$alkyl, $CH_2CONH_2$, $CH_2OH$, or $CH_2SH$, or a pharmaceutically, veterinary or agriculturally acceptable salt thereof.

Preferred compounds of formula (IV) have at least one of the following features:

Ar is phenyl or indolyl, $R^{31}$ is $CO_2H$ or $CONH_2$, $R^{32}$ is $C_{1-6}$alkyl, $CH_2CH_2CO_2H$, $CH_2CH_2CONH_2$, $CH_2CH_2OH$, or $CH—_2CH_2SH$, $R^{33}$ is $CH_2CO_2H$, $CH_2CONH_2$, $CH_2OH$, or $CH_2SH$.

In yet another embodiment, the metal chelating agent is a compound of formula (V):

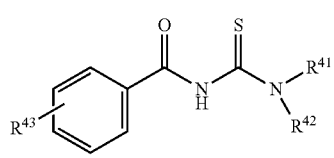
(V)

wherein $R^{41}$ and $R^{42}$ are independently selected from hydrogen, $C_{1-6}$alkyl, $C_{2-6}$alkenyl, $C_{2-6}$alkynyl or $R^{41}$ and $R^{42}$ taken together with the nitrogen to which they are attached form a 5 or 6 membered heterocyclic ring which is optionally substituted with one or more $C_{1-6}$alkyl, $C_{2-6}$alkenyl or $C_{2-6}$alkynyl groups; and $R^{43}$ is selected from hydrogen, $C_{1-6}$alkyl, $C_{2-6}$alkenyl, $C_{2-6}$alkynyl, hydroxy, $C_{1-6}$alkoxy, thiol, $C_{1-6}$alkylthiol, $CO_2H$, $CO_2C_{1-6}$alkyl, $SO_3H$, $SO_3C_{1-6}$alkyl, $NH_2$, $NHC_{1-6}$alkyl or $N(C_{1-6}$alkyl$)_2$;

or a pharmaceutically, veterinary or agriculturally acceptable salt thereof.

Preferred compounds of formula (V) have at least one of the following features:

$R^{41}$ and $R^{42}$ are independently selected from $C_{1-6}$alkyl or taken together with the nitrogen to which the are attached form a piperidine, piperazine, N-methylpiperazine or morpholine group;

$R^{43}$ is hydrogen, $C_{1-6}$alkyl, $C_{2-6}$alkenyl or $C_{2-6}$alkynyl.

In yet a further embodiment the metal chelating agent is a tetracyclic antibiotic selected from the group consisting of tetracycline, doxycycline or minocycline or a pharmaceutically, veterinary or agriculturally acceptable salt thereof.

In yet a further embodiment, the metal chelating agent is selected from 1-[(2S)-3-mercapto-2-methyl-1-oxopropyl]-L-proline (Captopril) or N-(alpha-rhamnopyranosyloxy-hydroxyphosphinyl)-L-leucyl-L-tryptophan (phosphoramidon), or a pharmaceutically, veterinary or agriculturally acceptable salt thereof.

As used herein, the term "alkyl" refers to a straight-chain or branched saturated hydrocarbon group and may have a specified number of carbon atoms. For example, $C_1$-$C_6$ as in "$C_1$-$C_6$alkyl" includes groups having 1, 2, 3, 4, 5 or 6 carbons in a linear or branched arrangement. Examples of suitable alkyl groups include, but are not limited to, methyl, ethyl, n-propyl, i-propyl, n-butyl, i-butyl, t-butyl, n-pentyl, 2-methylbutyl, 3-methylbutyl, 4-methylbutyl, n-hexyl, 2-methylpentyl, 3-methylpentyl, 4-methylpentyl, 5-methylpentyl, 2-ethylbutyl and 3-ethylbutyl.

As used herein, the term "alkenyl" refers to a straight-chain or branched hydrocarbon group having one or more double bonds between carbon atoms and may have a specified number of carbon atoms. For example, $C_2$-$C_6$ as in "$C_2$-$C_6$alkenyl" includes groups having 2, 3, 4, 5 or 6 carbon atoms in a linear or branched arrangement. Examples of suitable alkenyl groups include, but are not limited to, ethenyl, propenyl, isopropenyl, butenyl, pentenyl and hexenyl.

As used herein, the term "alkynyl" refers to a straight-chain or branched hydrocarbon group having one or more triple bonds between carbon atoms, and may have a specified number of carbon atoms. For example, $C_2$-$C_6$ as in "$C_2$-$C_6$alkynyl" includes groups having 2, 3, 4, 5 or 6 carbon atoms in a linear or branched arrangement. Examples of suitable alkynyl groups include, but are not limited to, ethynyl, propynyl, butynyl, pentynyl and hexynyl.

As used herein the term "halo" or "halogen" refers to fluorine (fluoro), chlorine (chloro), bromine (bromo) and iodine (iodo).

The term "alkyloxy" as used herein represents an alkyl group as defined above attached through an oxygen bridge. Examples of suitable alkyloxy groups include, but are not limited to, methoxy, ethoxy, n-propyloxy, i-propyloxy, n-butyloxy, i-butyloxy, t-butyloxy, n-pentyloxy and n-hexyloxy.

The term "alkylthio" as used herein represents an alkyl group as defined above attached through a sulfur bridge. Examples of suitable alkylthio groups include, but are not limited to, methylthio, ethylthio, propylthio, i-propylthio, butylthio, i-butylthio, t-butylthio, pentylthio, hexylthio.

The term "alkylene" as used herein represents a divalent alkyl group having a specified number of carbon atoms. For example, $C_{1-6}$alkylene includes —$CH_2$—, —$CH_2$—$CH_2$—, —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—.

The term "carbocyclic ring" as used herein refers to a 3 to 10 membered ring or fused ring system, in which all of the atoms that form the ring are carbon atoms. The $C_{3-10}$ carbocyclic ring may be saturated, unsaturated or aromatic. Examples of suitable carbocyclic rings include, but are not limited to, cyclopropyl, cyclobutyl, cyclopentyl, cyclopentenyl, cyclohexyl, cyclohexenyl, phenyl, naphthyl and tetrahydronaphthyl.

The term "heterocyclic ring" as used herein refers to a 3 to 10 membered ring or fused ring system in which at least one of the atoms that form the ring is a heteroatom. Preferably the heteroatom is selected from nitrogen, oxygen, sulfur and phosphorus. The $C_{3-10}$ heterocyclic ring may be saturated, unsaturated or aromatic. Examples of suitable heterocyclic rings include, but are not limited to, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazoyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

As used herein, the term "aryl" is intended to mean any stable, monocyclic or bicyclic carbon ring of up to 6 atoms in each ring, wherein at least one ring is aromatic. Examples of such aryl groups include, but are not limited to, phenyl, naphthyl and tetrahydronaphthyl.

The term "heteroaryl" as used herein, represents a stable monocyclic or bicyclic ring of up to 6 atoms in each ring, wherein at least one ring is aromatic and at least one ring contains from 1 to 4 heteroatoms selected from the group consisting of O, N and S. Heteroaryl groups within the scope of this definition include, but are not limited to, acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline.

The compounds of the invention may be in the form of pharmaceutically, veterinary or agriculturally acceptable salts. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benzenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium.

Basic nitrogen-containing groups may be quarternized with such agents as lower alkyl halide, such as methyl, ethyl, propyl, and butyl chlorides, bromides and iodides; dialkyl sulfates like dimethyl and diethyl sulfate; and others.

It will also be recognized that many compounds of the invention possess asymmetric centers and are therefore capable of existing in more than one stereoisomeric form. The invention thus also relates to compounds in substantially pure isomeric form at one or more asymmetric centers, e.g., greater than about 90% ee, such as about 95% or 97% ee or greater than 99% ee, as well as mixtures, including racemic mixtures, thereof. Such isomers may be prepared by asymmetric synthesis, for example using chiral intermediates, or by chiral resolution.

A number of metal chelating agents and metalloprotease inhibitors useful in the present invention can be obtained commercially from speciality chemical companies. Those not commercially available can be synthesized from commercially available starting materials using reactions known to those skilled in the art.

For example, substituted 2,29-bipyridyls and 1,10-phenanthrolines may be obtained from suitable halogenated 2,29-bipyridyls or 1,10-phenanthrolines. For example, 2,29-bipyridin-6,69-dicarboxylic acid may be obtained from 6,69-dibromo-2,29-dipyridyl by halogen-metal exchange with butyl lithium, treatment with dry ice and acidification [Buhleier et. al., *Chem. Ber.,* 1978, 111: 200-204]. Monosubstitution of a bipyridyl, for example with $CH_2CHNH_2(CO_2H)$ at the 6 position, can be obtained by treatment of 6-methyl-2, 29-bipyridyl with N-bromosuccinimide followed by alkylation with N-protectedglycine ester. The protecting groups can then be removed by acid hydrolysis, (Imperiali B. and Fisher S. L., *J. Org. Chem.*, 1992, 57: 757-759).

2,29-Dipyridyls can undergo nucleophilic substitution at the C6 and C4 positions to introduce substituents. This reaction is more favorable when a halogenated dipyridyl is used as the starting material. For example an amine may be introduced at C6 and/or C69 by using 6-mono or di-halogenated 2,29-dipyridyl and reacting this starting material with ammonia.

Bipyridyl-sulfonic acids can be prepared from 2,29-bipyridyl by heating with either oleum (a solution of sulfur trioxide in concentrated sulfuric acid) or mercury (II) sulfate/concentrated sulfuric acid at 300° C.

Unsymmetrically substituted bipyridyls can be obtained from symmetrical bipyridyls, for example, 6'-methyl-2,2'-bipyridyl-6-carboxylic acid can be prepared from 6,6'-dimethyl-2,2'-bipyridyl by oxidation with selenium dioxide followed by treatment with silver nitrate (Al-Saya et. al., *European J. Org. Chem.*, 2004, 173-182).

Compounds of formulae (III) and (IV) can be prepared from commercially available amino acids, for example phenylalanine and tryptophan, using known coupling reactions with amino acid carboxylic acids or amine groups (Jones J., *Amino Acid and Peptide Synthesis*, Oxford Chemistry Press, 1992). Suitable protection and deprotection steps may be required as known in the art and shown in Jones, 1992, Supra or Green T. W. and Wutz P., *Protecting Groups in Organic Synthesis*, John Wiley & Son, $3^{rd}$ Ed., 1999.

Thioureas of formula (V) may be prepared by reaction of a suitable benzamide with butyl lithium followed by thiophosgene. The resulting product can then be reacted with a suitable amine or amino acid as shown in Scheme 1.

Scheme 1

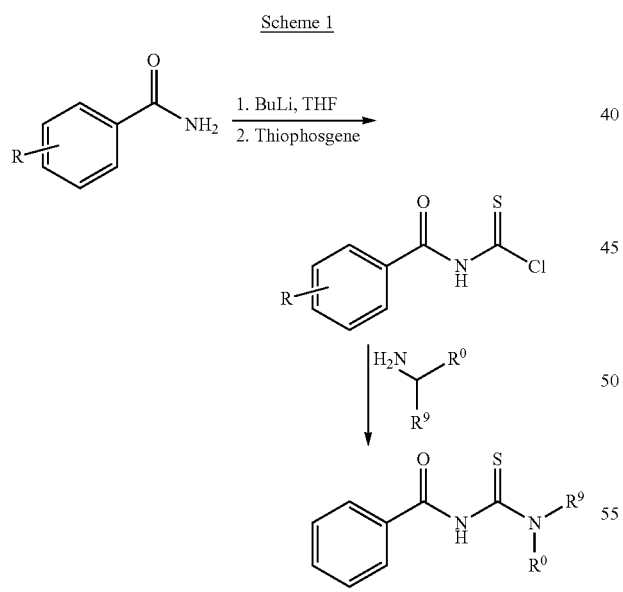

In the present specification, the term "ectoparasite" is taken to include any parasitic animal species that externally infests a host and that reproduces by egg laying. Preferred ectoparasites of the invention include a species from an order selected from the group consisting of Lepidoptera, Hemiptera, Orthoptera, Psocoptera, Hymenoptera, Isoptera, Coleoptera, Dictyoptera, Thysanoptera, Homoptera, Diptera, Anaplura, Malophaga, Siphonaptera, Arachnida and Phthiraptera.

Suitable ectoparasites that may be controlled using the methods of the present invention include:

(a) from the order of the lepidopterans (Lepidoptera), for example, *Adoxophyes orana, Agrotis ypsilon, Agrotis segetum, Alabama argillacea, Anticarsia gemmatalis, Argyresthia conjugella, Autographa gamma, Cacoecia murinana, Capua reticulana, Choristoneura fumiferana, Chilo partellus, Choristoneura occidentalis, Chrysodexis* Spp., *Cirphis unipuncta, Cnaphalocrocis medinalis, Crocidolomia binotalis, Crocidolomia pavonana, Cydia pomonella, Dendrolimus pini, Diaphania nitidalis, Diatraea grandiosella, Earias insulana, Elasmopalpus lignosellus, Epiphyas postvittana* (Walker), *Eupoecilia ambiguella, Feltia subterranea, Grapholitha funebrana, Grapholitha molesta, Helicoverpa* spp. such as *Helicoverpa armigera, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera scitella, Lithocolletis blancardella, Lobesia botrana, Loxostege sticticalis, Lymantria dispar, Lymantria monacha, Lyonetia clerkella, Manduca sexta, Malacosoma neustria, Mamestra brassicae, Mocis repanda, Operophthera brumata, Orgyia pseudotsugata, Ostrinia nubilalis, Pandemis heparana, Panolis flammea, Pectinophora gossypiella, Phthorimaea operculella, Phyllocnistis citrella, Pieris brassicae, Pieris rapae, Plathypena scabra, Platynota stultana, Plutella xylostella, Prays citri, Prays oleae, Prodenia sunia, Prodenia omithogalli, Pseudoplusia includens, Rhyacionia frustrana, Scrobipalpula absoluta, Sesamia inferens, Sparganothis pilleriana, Spodoptera frugiperda, Spodoptera littoralis, Spodoptera litura, Syllepta derogata, Synanthedon myopaeformis, Thaumatopoea pityocampa, Tortrix viridana, Trichoplusia ni, Tryporyza incertulas, Zeiraphera canadensis*; especially *Heliothis* spp., *Helicoverpa* Spp., *Crocidolomia pavonana, Pieris rapae, Phthorimaea operculella, Chrysodexis Spp.*, and *Plutella xylostella;*

(b) from the order of the hemipterans (Hemiptera), for example, *Aphis, Bemisia, Phorodon, Aeneolamia, Empoasca, Parkinsiella, Pyrilla, Aonidiella, Coccus, Pseudococcus, Helopeltis, Lygus, Dysdercus, Oxycarenus, Nezara, Aleyrodes, Triatoma, Psylla, Myzus, Megoura, Phylloxera, Adelges, Nilaparvata, Nephotettix* or *Cimwx* spp.;

(c) from the order of the orthopterans (Orthoptera), for example, *Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca peregrina, Stauronotus maroccanus, Schistocerca gregaria;*

(d) from the order of the psocopterans (Psocoptera), for example, *Peripsocus* spp.;

(e) from the order of the hymenopterans (Hymenoptera), for example, *Athalia rosae, Atta cephalotes, Atta sexdens, Atta texana, Hoplocampa minuta, Hoplocampa testudinea, Iridomyrmes humilis, lridomyrmex purpureus, Monomorium pharaonis, Solenopotes capillatus, Solenopsis geminata, Solenopsis invicta, Solenopsis richteri, Technomyrmex albipes;*

(f) from the order of the termites (Isoptera), for example, *Calotermes flavicollis, Coptotermes* spp, *Leucotermes flavipes, Macrotermes subhyalinus, Nasutitermes* spp such as *Nasutitermes walkeri, Odontotermes formosanus, Reticulitermes lucifugus, Termes natalensis;*

(g) from the order of the beetles (Coleoptera), for example, *Anthonomus grandis, Anthonomus pomorum, Apion vorax, Atomaria linearis, Blastophagus piniperda, Cassida nebulosa, Cerotoma trifurcata, Ceuthorhynchus assimilis, Ceuthorhynchus napi, Chaetocnema tibialis, Conoderus vespertinus, Crioceris asparagi, Dendroctonus refipennis, Diabrotica longicomis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips. typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllopertha horticola, Phyllophaga sp., Phyllotreta chrysocephala, Phyllotreta nemorum, Phyllotreta striolata, Popillia japonica, Psylliodes napi, Scolytus intricatus, Sitona lineatus;*

(h) from the order Dictyoptera, for example, from the families Polyphagidae, Bladberidae, Blattidae, Epilampridae, Chaetecsidae, Metallycidae, Mantoididae, Amorphoscelidae, Eremiaphilidae, Hymenopodidae, Mantidae and Empusidae;

(i) from the order of the thrips (Thysanoptera), for example, *Frankliniella fusca, Frankliniella occidentalis, Frankliniella tritici, Haplothrips tritici, Heliothrips haemorrhoidalis, Scirtothrips citri, Thrips oryzae, Thrips palmi, Thrips tabaci;*

(j) from the order of the homopterans (Homoptera), for example, *Acyrthosiphon onobrychis, Acyrthosiphon pisum, Adelges laricis, Aonidiella aurantii, Aphidula nasturtii, Aphis fabae, Aphis gossypii, Aphis pomi, Aulacorthum solani, Bemisia tabaci, Brachycaudus cardui, Brevicoryne brassicae, Dalbulus maidis, Dreyfusia nordmannianae, Dreyfusia piceae, Dysaphis radicola, Empoasca fabae, Eriosoma lanigerum, Laodelphax striatella, Macrosiphum avenae, Macrosiphum euphorbiae, Macrosiphon rosae, Megoura viciae, Metopolophium dirhodum, Myzus persicae, Myzus cerasi, Nephotettix cincticeps, Nilaparvata lugens, Perkinsiella saccharicida, Phorodon humuli, Psylla mali, Psylla piri, Psylla pyricola, Rhopalosiphum maidis, Schizaphis graminum, Sitobion avenae, Sogatella furcifera, Toxoptera citricida, Trialeurodes abutilonea, Trialeurodes vaporariorum, Viteus vitifolii;*

(k) from the order of the dipterans (Diptera), for example, *Anastrepha ludens, Ceratitis capitata, Contarinia sorghicola, Dacus cucurbitae, Dacus oleae, Dasineura brassicae, Delia coarctata, Delia radicum, Hydrellia griseola, Hylemyia platura, Liriomyza sativae, Liriomyza trifolii, Lucilia* Sp., *Mayetiola destructor, Musca* sp., *Orseolia oryzae, Oscinella frit, Pegomya hyoscyami, Phorbia antiqua, Phorbia brassicae, Phorbia coarctata, Rhagoletis cerasi, Rhagoletis pomonella;*

(l) from the order Anaplura, for example, *Pthirus pubis, Pediculus humanus capitis, Pediculus humanus humanus;*

(m) from the order Mallophaga, for example, from the genera *Bovicola,* such as *Bovicola ovis* or *Bovicola bovis, Damalania, Trichodectus* and *Menopon;* especially *Bovicola ovis* or *Bovicola bovis;*

(n) from the order of the siphonapterans (Siphonaptera), for example, *Ctenocephalides* or *Pulex* spp.

(o) from the order Arachnida, for example, *Ixodes holocyelus, Boophilus microplus, Rhipicephalus sanguine us, Sarcoptes scabiei* var. *humani, Sarcoptes scabiei canis, Sarcoptes scabiei suis, Sarcoptes scabiei bovis, Psoroptes ovis* and *Dermatophagoides* spp., especially *Sarcoptes scabiei* var. *humani, Sarcoptes scabiei canis, Sarcoptes scabiei suis, Sarcoptes scabiei bovis, Psoroptes ovis* and *Dermatophagoides* spp.

(p) from the order of Phthiraptera, for example, *Linognathus vituli* and *Haematopinus eurysternus.*

Especially preferred ectoparasites that infest plants include *Helicoverpa* spp. such as *Helicoverpa armigera* (Budworms), *Crocidolomia pavonana* (Cabbage cluster caterpillar), *Pieris rapae* (Cabbage white butterfly), *Phthorimaea operculella* (Potatoe moth), *Chrsyodexis* spp. (Tobacco loopers), *Plutella xylostella* (Diamondback moth) and *Epiphyas postvittana* (Walker) (Light brown apple moth).

Especially preferred ectoparasites that infest domestic animals include *Bovicola ovis* (Sheep louse), *Bovicola bovis, Haematopinus eurysternus* (short-nosed cattle louse), *Linognathus vituli* (long nosed cattle louse), *Solenopotes capillatus* (tubercule-bearing louse), *Sarcoptes scabiei canis* (mange), *Sarcoptes scabiei suis, Sarcoptes scabiei bovis* and *Psoroptes ovis.*

Especially preferred ectoparasites that infest humans include *Pthirus pubis, Pediculus humanus capitus, Pediculus humanus humanus, Sarcoptes scabiei* var. *humani* and *Dermatophgoides* spp.

In one embodiment, the ectoparasite egg which is prevented from hatching by the present invention is selected from the group consisting of louse, flea, tick, fly, mite and other biting or blood-sucking ectoparasite eggs. In one embodiment, the ectoparasite egg is a louse egg, more preferably head louse egg. Lice are a parasite that feed on animal skin and blood and they deposit their digestive juices and faecal material into the skin. These materials, as well as the puncture wound itself, cause skin irritation and lesions from the resulting scratching, and can cause a serious infection with ganglionic inflammation. Lice are also vectors of certain diseases, such as exanthematic or epidemic typhus and recurrent fever. The adult female louse has a life span of about one month and can lay up to ten eggs a day. Lice that infect humans may include the species of crab louse (*Pthirus pubis*) and the separate species Pediculus humanus which is composed of two subspecies, *Pediculus humanus capitis* or head lice and *Pediculus humanus humanus* or clothing lice (Busvine, *Antenna,* 1993, 17: 196-201). The above subspecies of lice are closely related and are known to successfully interbreed (Busvine, *Cutaneous Infestations and Insect Bites,* 1985, 163-174).

The head louse *Pediculus humanus* var. *capitis,* is a host-specific ectoparasite that lives exclusively on human heads and feeds via sucking blood from the scalp. Following a blood meal, mature adult female lice will lay up to 10 eggs close to the scalp over a 24 hr period. The eggs are attached firmly to the hair shaft via a glue. Seven to ten days post laying depending on temperature and humidity, the eggs will hatch and the newly emerged nymphs begin to feed. The nymphs progress through three moults ($1^{st}$ instar, $2^{nd}$ instar, $3^{rd}$ instar) with each moult taking between 3-5 days to complete. Following the final moult the adult male or female emerges with mating taking place as early as two days later. Within hours of feeding, eggs will be produced and the cycle continues. The entire life cycle from egg to egg takes approximately 20-30 days to complete depending on conditions of warmth and humidity. Following egg hatching the egg shell remains attached to the hair shaft and will gradually move away from the scalp as the hair lengthens. Hatched eggs (nits) are relatively easily detected due to their refractive nature appearing white under artificial light, in contrast unhatched eggs are a light pale brown in color enabling them to blend in to most hair colors and therefore making them more difficult to detect.

In another embodiment, the ectoparasite egg which is prevented from hatching by the present invention is one that infests a plant host. In a preferred embodiment, the ectoparasite egg is a budworm egg, a caterpillar egg, a butterfly egg or a moth egg. Budworms, caterpillars, butterflies and moths and their larvae feed on valuable crop plants such as cotton, oil seed crops such as canola, ornamental plants, flowers, fruit trees, cereal crops, vine crops, root crops, pasture crops, tobacco, pulses and vegetables, especially *Brassica* crops such as cauliflower and broccoli, cotton, maize, sweet corn, tomatoes, tobacco and pulses such as soybeans, navy beans, mungbeans, pigeon peas and chickpeas.

The diamondback moth (*Plutella xylostella*) larvae feed on all plants in the mustard family, including canola and mustard, vegetable crops such as broccoli, cauliflower and cabbage and also on several greenhouse plants. Normally the diamondback moth takes about 32 days to develop from egg to adult. However, depending on food and weather conditions, a generation may take from 21 to 51 days to complete. Adult female moths lay an average of 160 eggs over a lifespan of about 16 days. A female will lay eggs at night and will lay the largest number of eggs the first night after emergence from the pupa. The eggs are small, spherical or oval and yellowish-white and are glued to the upper or lower surfaces of a leaf either singly or in groups of two or three. The eggs are usually laid along the veins of the leaf where the leaf surface is uneven. The eggs hatch in about five to six days. After hatching, the larvae burrow into the leaf and begin eating the leaf tissue internally. After about a week, the larvae exit from the leaf and feed externally. The larvae moult three times over 10 to 21 days and at maturity are about 12 mm long. The larvae pupate in delicate, open-mesh cocoons attached to the leaves and the pupal stage lasts from 5 to 15 days.

Budworms such as corn ear worm, tomato grub, tobacco budworm and cotton Bollworm are serious pests in a number of crops such as sunflowers, zucchini, beans, peppers, alfalfa, potatoes, leeks, cotton, maize, plums, citrus plants, tomatoes, tobacco and lettuce, and flowers such as geraniums and pinks. Budworms occur in many regions of the world and in temperate climates may have 2-3 generations per season with pupae overwintering in the soil. In tropical regions, the budworms may continue to be active year round. Eggs are small (~0.5 mm in diameter) and dome shaped with a slightly flattened bottom. Eggs are usually laid singularly near buds or flowering parts or on leaves. An adult may lay 500-3000 eggs. The eggs hatch after only three days at 25° C. or longer at cooler temperatures, for example, 9 days at 17° C. The larval feeding period is about 19 to 26 days under favorable temperature and feeding conditions and when fully developed the larvae move to the soil to pupate. The pupal period generally lasts from 8 to 21 days although diapausing pupae can overwinter in soil in temperate regions.

Light brown apple moth (*Epiphyas postvittana* (Walker)) larvae cause damage to the leaves and fruit of apples, pears, grapes, citrus varieties, black and red currants, kiwifruit, hops, red and white clovers, lucerne, tree lupin, plantain, tutu, gorse, chrysanthemum, michaelmas daisy and other flowering plants, shrubs, especially acacias and conifers in the young stages of growth. The moth may have 2-4 generations annually in a temperate climate. Eggs are laid in clusters of 3 to 150 eggs on leaves or fruit, which hatch to provide the larvae.

In one embodiment of the present invention, the methods and compositions of the invention are to cure a subject of lice by inhibiting hatching of louse eggs. The present applicants have identified metal chelating agents and metalloprotease inhibitors as an effective agent for inhibiting ectoparasite louse egg hatching. The use of metal chelating agents or metalloprotease inhibitors for inhibiting ectoparasite louse egg hatching has the advantage of preventing breeding cycles of ectoparasites thereby controlling ectoparasite infestation.

In another embodiment of the present invention, the methods and compositions of the invention are to prevent larval infestation of plants by inhibiting ectoparasite egg hatching. The present applicants have identified metal chelating agents and metalloprotease inhibitors as an effective agent for inhibiting ectoparasite egg hatching that results in larvae that feed on commercially valuable plants. The use of metal chelating agents or metalloprotease inhibitors for inhibiting ectoparasite egg hatching has the advantage of preventing breeding cycles of ectoparasites that produce larvae that feed on commercially valuable plants thereby controlling ectoparasite infestation of the commercially valuable plants.

The term "metalloprotease" as used herein is taken to refer to a protease involved in ectoparasite egg hatching or development, wherein the protease has an active metal ion that acts as a catalyst. Preferably, the metalloprotease contains a zinc ion that participates in catalysis by polarizing a water molecule to attack a substrate-peptide bond. More preferably, the metalloprotease is sensitive to metal chelating agents that are capable of blocking their activity. The metalloprotease may be involved in inducing egg hatching by acting on the operculum of an egg to facilitate egg hatching. Suitable metalloproteases involved in ectoparasite egg hatching can include endoproteases (enzymes that cleave within the peptide chain) and exoproteases (enzymes that cleave amino acid(s) from the termini of peptides). Exoproteases can further be categorized as carboxyproteases (which cleave amino acid(s) from the C terminus) or aminopeptidase (which cleave amino acids from the N terminus). Metallocarboxyproteases require a bivalent cation (usually $Zn^{2+}$) for activity, while aminopeptidases are generally classified according to their dependence on metal ions ($Zn^{2+}$ or $Mg^{2+}$). They exist in both free and membrane-bound forms and favor activity at high (8-10) pH. One method of detecting metalloproteases associated with egg hatching can involve collecting either the fluid surrounding the developing embryo at the time of egg hatching or by washing the empty egg shells shortly after egg hatching and analyzing the sample for the presence of proteases using gelatine substrate SDS-PAGE analysis. Having shown the presence of proteolytic activity from the sample it is then possible to incubate the sample in the presence of a metalloprotease inhibitor, for example, 1,10-phenantholine, and then reanalyze the treated sample to determine if the activity of the proteases extracted from the egg have been inhibited. Having shown inhibition of the activity of the metalloprotease(s) obtained from the hatched egg, it is then possible to expose unhatched eggs to the same inhibitor and assess whether inhibition of egg hatching occurs. Metalloproteases involved in egg hatching may also be identified by identification of a gene encoding a metalloprotease, silencing that gene and showing that the egg is unable to hatch by methods known to those skilled in the art.

The phrase "inhibiting hatching of an ectoparasite egg" as used herein is taken to mean that hatching of an ectoparasite egg is prevented. In the present invention an ectoparasite egg is exposed to a metal chelating agent or a metalloprotease inhibitor that is capable of preventing egg hatching when compared to an untreated ectoparasite egg. Egg hatching is characterized by the hatchflap or operculum of an egg opening and shortly thereafter the emergence of a larvae or nymph. In the case of lice, the head appears first followed by the thorax to which the legs are attached. Finally, the abdomen emerges and the nymph moves free from the egg. In the case of a moth or butterfly egg, the egg hatches and a larva emerges. Egg hatching is taken to exclude damage or accidental breakage of an eggshell.

Preferably, the metal chelating agent or metalloprotease inhibitor is a compound capable of inhibiting egg hatching when it is applied to the egg at any time between laying and hatching.

The ectoparasite egg is preferably present on, but not limited to, a host organism, such as on the skin, hair, coat or fleece of an animal or skin or hair such as head hair of a human. In alternative embodiments of the invention the ectoparasite egg may be present on host plants including cereal crops, fruit trees, cotton, oil seed crops, ornamental plants, flowers, vine crops, root crops, pasture plants and vegetables, or other breeding sites, such as, but not limited to, houses and buildings, enclosures for domestic and farming animals, carpets, bedding such as sheets and blankets, curtains and furniture.

According to the present invention, the ectoparasite egg may be exposed to a metal chelating agent or a metalloprotease inhibitor by any suitable means. A person skilled in the art will appreciate that these means may vary widely, depending upon whether the inhibitor is to be applied to a host, such as a plant or animal including a human, or various other breeding sites, and depending on the nature and type of ectoparasite targeted. Suitable means for exposing ectoparasite eggs present on animals to metal chelating agents or metalloprotease inhibitors, include, but are not limited to, direct topical application, such as by dipping or spraying, implants, delayed release formulations or devices. Where the invention is applied to humans, formulations suitable for topical application include but are not limited to sprays, aerosols, shampoos, mousses, creams and lotions, and formulations suitable for internal application include but are not limited to tablets, capsules or liquid formulations. In some situations parenteral administration by injection may be the most suitable means of treatment for humans or animals. Where the metal chelating agent or metalloprotease inhibitor is to be applied to plants, suitable means include but are not limited to sprays, dusts, pellets, liquids or aerosols. The method of the invention also encompasses the concurrent or successive use of two or more metal chelating agents or metalloprotease inhibitors or the use of one or more metal chelating agents and/or metalloproteases in conjunction concurrently or successively with other known agents that control ectoparasites.

In yet another aspect of the invention, the methods and compositions may include other ectoparasiticides that control hatching, larvae, nymphs or adult ectoparasites. For example, suitable ectoparasiticides which may be used in conjunction, either simultaneously, separately or sequentially, with the metal chelating agents or metalloprotease inhibitors of the present invention include macrocyclic lactones such as spinosad, botanical insecticides, carbamate insecticides, dessicant insecticides, dintrophenol insecticides, fluorine insecticides, formamidine insecticides such as armitraz, fumigant insecticides, inorganic insecticides, insect growth regulators, (including chitin synthesis inhibitors, juvenile hormone mimics, juvenile hormones, moulting hormone agonists, moulting hormone antagonists, moulting hormones, moulting inhibitors), nicotinoid insecticides, organochlorine insecticides, organophosphorus insecticides, heterocyclic organothiophosphate insecticides, phenyl organothiophosphate insecticides, phosphonate insecticides, phosphonothioate insecticides, phosphoramidate insecticides, phosphoramidothiate insecticides, phosphorodiamide insecticides, oxadiazine insecticides, phthalimide insecticides, pyrazole insecticides, pyrethroid insecticides, pyrimidinamine insecticides, pyrrol insecticides, tetronic acid insecticides, thiourea insecticides and urea insecticides including agents described in EP 0191236, U.S. Pat. No. 5,288,483 and U.S. Pat. No. 6,727,228. Other useful insecticides include dimethicone copolyols, such as those described in U.S. Pat. No. 6,663,876 and U.S. Pat. No. 6,607,716, which have low toxicity. The advantage of such a combination is that only one application may be required to control the ectoparasite over all of its life cycle.

The metal chelating agent or the metalloprotease inhibitor may be applied to the hair or skin of a host when the host is a human or animal, preferably in a region that is infested with an ectorparasite. The ectoparasite infestation may preferably be due to ectoparasites selected from the group consisting of lice, fleas, ticks, flies, mites and other biting or blood-sucking ectoparasites, and combinations thereof, especially ectoparasite infestations due to lice. The metal chelating agent or the metalloprotease inhibitor may be applied topically in the form of ointments, aqueous compositions including solutions and suspensions, creams, lotions, aerosol sprays or dusting powders. When the host is a plant, the ectoparasite infestation is preferably due to ectoparasites selected from budworms, caterpillars, butterflies or moths. The metal chelating agent or the metalloprotease inhibitor may be applied topically, for example, in the form of a spray or dust.

The term "effective amount" means a concentration of at least one metal chelating agent or at least one metalloprotease inhibitor sufficient to provide treatment or prevention of ectoparasite infestation in a host. The effective amount of a metal chelating agent or metalloprotease inhibitor used in the methods of the present invention may vary depending on the host and the type and level of ectoparasite infestation. In one embodiment, the metal chelating agent or metalloprotease inhibitor is applied to the scalp of a person suffering from head lice infestation and are left on the treated person for a period of time to prevent hatching of the louse eggs. Preferably the period of time is between 5 and 15 minutes. The metal chelating agent or metalloprotease inhibitor is preferably used at a concentration of between about 0.0001 mM to 1 M, preferably 0.01 mM and 100 mM, more preferably in the range of 0.1 mM and 30 mM. The effective amount depends on the metal chelating agent or metalloprotease used. However, some dipyridyl compounds may suitably be applied in the range of 5 mM to 15 mM, especially at a level of about 10 mM. Since a significant number of mammalian proteases require zinc for their activity and may be effected by metal chelating agents and/or metalloprotease inhibitors, it would be necessary to ensure that the metal chelating agent or metalloprotease inhibitor was used in a safe and effective amount and is preferably specifically targeted to ectoparasite eggs.

In another embodiment, the metal chelating agent or metalloprotease inhibitor is applied to a commercially valuable plant to prevent hatching of ectoparasite eggs. The metal chelating agent or metalloprotease inhibitor may be applied directly to eggs which are present on the leaves, buds, stems, flowers or fruit of a plant by spray application, brushing on or dusting. Suitable compositions include emulsifiable concentrates, directly sprayable or dilutable solutions, dilute emulsions, wettable powders, soluble powders, dusts or granules. The metal chelating agent or metalloprotease inhibitor is preferably used at a concentration of between about 0.0001 mM to 1M, preferably 0.01 mM and 100 mM, more preferably in the range of 0.1 mM and 30 mM. The effective amount depends on the metal chelating agent or metalloprotease used.

However, some dipyridyl compounds may suitably be applied in the range of 5 mM to 15 mM, especially at a level of about 10 mM.

The host treated by the methods of the invention may be selected from, but is not limited to, the group consisting of humans, sheep, cattle, horses, pigs, poultry, dogs and cats. The methods of treatment or prevention of the present invention may be applicable to plants and or other breeding sites of ectoparasites. Plants treated by the methods of the invention are preferably selected from the group consisting of cotton, oil seed crops such as canola, ornamental plants such as shrubs, flowers such as chrysanthemum, michaelmas daisy, geraniums and pinks, fruit trees such as apples, pears, plums, kiwifruit, currants and citrus varieties for example, lemons, oranges, limes and grapefruit, cereal crops such as maize and sweet corn, vine crops such as grapes, root crops, pasture plants such as red and white clover, lucerne and lupins, and vegetables such as *brassica* crops, for example, broccoli and cauliflower, cabbage, tomatoes, zucchini, leeks, lettuce and beans as well as pulses such as navy beans, soybeans, mungbeans, pigeon peas and chickpeas.

The compositions of the present invention may be formulated as solutions and emulsions. Suitable excipients, such as emulsifiers, surfactants, stabilizers, dyes, penetration enhancers and anti-oxidants may also be present in the compositions. Suitable carriers that may be added in the compositions can include, water, salt solutions, alcohols, polyethylene glycols, gelatine, lactose, magnesium sterate and silicic acid. The compositions may include sterile and non-sterile aqueous solutions. In one embodiment, the compositions are in a soluble form and the metal chelating agent or metalloprotease inhibitor is diluted in a soluble sterile buffered saline or water solution. The compositions can also be formulated as suspensions in aqueous, non-aqueous or mixed media. Aqueous suspensions may further contain substances that increase the viscosity of the suspension and may also contain stabilizers. The solutions may also contain buffers, diluents and other suitable additives. The compositions can include other adjunct components that are compatible with the activity of the metal chelating agent or metalloprotease inhibitor. The compositions of the present invention may be formulated and used as foams, emulsions, microemulsions, shampoos, mousses, creams and jellies. The formulations of the above compositions described would be known to those skilled in the field of ectoparasiticides.

The active ingredients according to the invention can be used for inhibiting hatching of ectoparasite eggs on plants, mainly on crops of useful plants and ornamentals in agriculture, in horticulture and in silviculture, or on parts of such plants, such as fruits, flowers, foliage, stalks, tubers or roots, and in some cases even parts of plants which are formed at a later point in time are afforded protection against these pests. In these compositions, the active ingredient is employed together with at least one of the auxiliaries conventionally used in the art of formulation, such as extenders, e.g., solvents or solid carriers, or such as surface-active compounds (surfactants).

Examples of suitable solvents are: non-hydrogenated or partially hydrogenated aromatic hydrocarbons, preferably the fractions $C_8$-$C_{12}$ of alkylbenzenes, such as xylene mixtures, alkylated naphthalenes or tetrahydronaphthalene, aliphatic or cycloaliphatic hydrocarbons such as paraffins or cyclohexane, alcohols such as methanol, ethanol, propanol or butanol, glycols and their ethers and esters such as propylene glycol, dipropylene glycol ether, hexylene glycol, ethylene glycol, ethylene glycol monomethyl ether or ethylene glycol monoethyl ether, ketones such as cyclohexanone, isophorone or diacetone alcohol, strongly polar solvents such as N-methylpyrrolid-2-one, N-methyl-pyrrolidine, dimethyl sulfoxide or N,N-dimethylformamide, water, free or epoxidized rapeseed, castor, coconut or soya oil, and silicone oils.

Solid carriers which are used for example for dusts and dispersible powders are, as a rule, ground natural minerals, such as calcite, talc, kaolin, montmorillonite or attapulgite. To improve the physical properties, it is also possible to add highly-disperse silicas or highly-disperse absorptive polymers. Suitable particulate adsorptive carriers for granules are porous types, such as pumice, brick grit, sepiolite or bentonite, and suitable non-sorptive carrier materials are calcite or sand. Moreover, a large number of granulated materials of inorganic or organic nature can be used, in particular dolomite or comminuted plant residues.

Suitable surface-active compounds are, depending on the nature of the active ingredient to be formulated, non-ionic, cationic and/or anionic surfactants or surfactant mixtures which have good emulsifying, dispersing and wetting properties. The surfactants listed below are only to be considered as examples; many more surfactants conventionally used in the art of formulation and suitable in accordance with the invention are described in the relevant literature.

Suitable non-ionic surfactants are primarily polyglycol ether derivatives of aliphatic or cycloaliphatic alcohols, of saturated or unsaturated fatty acids and alkylphenols which can contain 3 to 30 glycol ether groups and 8 to 20 carbon atoms in the (aliphatic) hydrocarbon radical and 6 to 18 carbon atoms in the alkyl radical of the alkylphenols. Also suitable are water-soluble polyethylene oxide adducts with polypropylene glycol, ethylenediaminopolypropylene glycol and alkylpolypropylene glycol having 1 to 10 carbons in the alkyl chain and 20 to 250 ethylene glycol ether and 10 to 100 propylene glycol ether groups. The above-mentioned compounds normally contain 1 to 5 ethylene glycol units per propylene glycol unit. Examples which may be mentioned are nonylphenylpolyethoxyethanols, castor oil polyglycol ethers, polypropylene/polyethylene oxide adducts, tributylphenoxypolyethoxyethanol, polyethylene glycol and octylphenoxypolyethoxyethanol. Also suitable are fatty acid esters of polyoxyethylene sorbitan, such as polyoxyethylene sorbitan trioleate.

The cationic surfactants are mainly quaternary ammonium salts which have, as substituents, at least one alkyl radical of 8 to 22 carbon atoms and, as further substituents, lower alkyl, benzyl or lower hydroxyalkyl radicals which may be halogenated. The salts are preferably in the form of halides, methylsulfates or ethylsulfates. Examples are stearyltrimethylammonium chloride and benzyldi(2-chloroethyl) ethylammonium bromide.

Suitable anionic surfactants can be both water-soluble soaps and water-soluble synthetic surface-active compounds. Soaps which are suitable are the alkali metal salts, alkaline earth metal salts and unsubstituted or substituted ammonium salts of higher fatty acids ($C_{10}$-$C_{22}$), such as the sodium or potassium salts of oleic or stearic acid, or of natural fatty acid mixtures which can be obtained, for example, from coconut or tall oil; or fatty acid methyltaurinates. However, synthetic surfactants, in particular fatty sulfonates, fatty sulfates, sulfonated benzimidazole derivatives or alkylarylsulfonates, are used more frequently. As a rule, the fatty sulfonates and fatty sulfates exist as alkali metal salts, alkaline earth metal salts or unsubstituted or substituted ammonium salts and generally have an alkyl radical of 8 to 22 carbon atoms, alkyl also including the alkyl moiety of acyl radicals. Examples of fatty sulfonates and fatty sulfates include the sodium or calcium salt of lignosulfonic acid, of the dodecylsulfuric ester or of a fatty alcohol sulfate mixture prepared with natural fatty acids. This group also includes the salts of the sulfuric esters and sulfonic acids of fatty alcohol/ethylene oxide adducts. The sulfonated benzimidazole derivatives preferably contain 2 sulfo groups and one fatty acid radical having approximately 8 to 22 carbon atoms. Examples of alkylarylsulfonates are the sodium, calcium or triethanolammonium salts of dodecylbenzenesulfonic acid, of dibutylnaphthalenesulfonic acid or of a naphthalenesulfonic acid/formaldehyde condensate. Also suitable are corresponding phosphates, such as salts of the phosphoric ester of a p-nonylphenol(4-14)ethylene oxide adduct, or phospholipids.

In a preferred embodiment, the composition comprises a metal chelating agent at a concentration of about 0.0001 mM to 1 M, preferably between 0.1 mM to 100 mM, more preferably in the range of 0.1 mM to 30 mM. Compositions containing some metal chelating agents or metalloprotease inhibitors, for example, the dipyridyl compounds, may preferably contain between 5 and 15 mM of compound, especially at a level of about 10 mM.

A compound which inhibits hatching of an ectoparasite egg, may be identified using a method comprising assessing the ability of the compound to inhibit a metalloprotease present in the ectoparasite egg.

The effect of the compound on the activity of the metalloprotease may be assessed in a number of ways, however, in general the assessment preferably involves comparison of metalloprotease enzyme activity in the presence and absence of the test compound. One method of detecting metalloproteases associated with egg hatching can involve collecting either the fluid surrounding the developing embryo at the time of egg hatching or by washing the empty egg shells shortly after egg hatching and analyzing the sample for the presence of proteases using gelatine substrate SDS-PAGE analysis. Having shown the presence of proteolytic activity from the sample it is then possible to incubate the sample in the presence of a metalloprotease inhibitor, for example, 1,10-phenantholine, and then reanalyze the treated sample to determine if the activity of the proteases extracted from the egg have been inhibited. Having shown inhibition of the activity of the metalloprotease obtained from the hatched egg, it is then possible to expose unhatched eggs to the same inhibitor and assess whether inhibition of egg hatching occurs. Metalloproteases involved in egg hatching may also be identified by identification of a gene encoding a metalloprotease, silencing that gene and showing that the egg is unable to hatch by methods known to those skilled in the art. The method may further comprise testing the compound in a biological ectoparasite egg hatching assay.

A suitable biological ectoparasite egg hatching assay preferably comprises exposing a control sample of ectoparasite eggs to a control buffer solution whilst at the same time exposing a test sample of ectoparasite eggs to a solution comprising a test compound.

A compound that is effective in inhibiting ectoparasite egg hatching is identified when egg hatching is observed in the control sample and a lower level of hatching is observed in the test sample. In the biological egg hatching assay of the present invention, the ectoparasite eggs are selected from the group consisting of louse, flea, tick, fly, mite and other biting or blood-sucking ectoparasite eggs or an ectoparasite egg which infests plants such as budworms, caterpillars, moths and butterflies. In one embodiment, the sample of ectoparasite eggs are lice eggs and the egg samples (control and test samples) used are no more than post 6-7 days after being laid. Preferably, the egg samples used are no more than 1 day after being laid.

The control buffer solution may include, but is not limited to, sterile phosphate buffered saline or water. The compound tested is preferably a metal chelating agent and/or a metalloprotease inhibitor. In the biological egg hatching assay egg hatching is observed when the hatchflap or operculum of the egg opens and shortly thereafter the larvae or nymph begins to emerge. In the case of lice, the head appears first followed by the thorax to which the legs are attached. Finally, the abdomen comes out and the nymph moves free from the egg. In the case of head lice, the eggshell then remains cemented to the hair shaft.

In another aspect of the invention there is provided a use of at least one metal chelating agent in the manufacture of a composition for inhibiting hatching of an ectoparasite egg or for treating or preventing ectoparasite infestation, wherein the metal chelating agent is a compound comprising at least two heteroatoms able to simultaneously coordinate with a metal ion, at least one of the two heteroatoms being selected from nitrogen, sulfur, oxygen and phosphorus, wherein the compound comprises at least one carbocyclic ring substituted with at least one heteroatom and/or with a substituent containing at least one heteroatom, or the compound comprises at least one heterocyclic ring containing at least one heteroatom, wherein said heterocyclic ring is optionally substituted with at least one heteroatom and/or with a substituent containing at least one heteroatom. In one embodiment, the ectoparasite egg is one infesting a plant host. In another embodiment, the ectoparasite egg is one infesting a domesticated animal. In yet another embodiment, the ectoparasite egg is one infesting a human.

Also encompassed by the present invention are agents comprising at least one metal chelating agent and/or at least one metalloprotease inhibitor as described herein, for inhibiting hatching of an ectoparasite egg or for treating or preventing ectoparasite infestation.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention will hereinafter be described by way of the following non-limiting Figures and Examples.

EXAMPLES

Example 1

Assessment of the Mechanism of Lice Egg Hatching

The mechanism of lice egg hatching was assessed under a dissecting microscope. Female clothing lice were fed for half an hour on a rabbit before being transferred to a petri dish containing human hair. The petri dish was then placed in an incubator at 32° C.; 42% relative humidity. Within 5 hours of feeding the female lice begin to lay their eggs. Each female lays up to 10 eggs at a sitting. The eggs develop over the next 7-9 days. Within the last 12 hrs prior to hatching the following changes were observed. The eyes of the developing embryo could be clearly detected inside the egg with the developing embryo orientated so that it has its head is adjacent to the hatch flap or operculum. The embryo can be observed moving within the egg. Hatching takes place when the operculum opens and shortly thereafter the embryo begins to emerge. The head appears first followed by the thorax to which the legs are attached. Finally, the abdomen comes out and the nymph moves free from the egg that remains cemented to the hair. There are no obvious structures associated with the head of the newly emerged nymph visible under light microscopy, that would facilitate hatching (i.e., no egg tooth is present). This observation suggests that while physical movement of the nymph within the egg probably contributes to egg hatching, other specific biochemical events are involved.

Example 2

Detection of Protease Activity in Lice Egg Extracts

Within 12 hours of hatching 50 body lice eggs (*Pediculus humanus humanus*) were removed from the hair and placed in a 1 ml eppendorf tube. 20 μL of distilled water was added to the unhatched eggs and the preparation incubated for 30 minutes at 32° C. The 20 μl was recovered, freeze dried and stored at −70° C. A number of other samples were also collected as described. Hair samples from which unhatched lice eggs had been removed were also collected and incubated as described above. In addition, a sample of unhatched eggs and a sample of hair from which lice eggs had been removed were collected 7 days post laying (within 24 hrs of egg hatching). Both samples were washed in 10 mls of a 1% solution of sodium hypochlorite for 1 minute followed by a 5×1 minute washes in 25 mls in distilled water to remove the hypochlorite. These samples were then incubated in 20 μl of distilled water as described above. In addition, a group of 25 lice eggs that were within 24 hours of hatching, were pretreated with 1% sodium hypochlorite, washed as described above and left to hatch. Within 1-2 hours after hatching the empty egg shells were incubated in 20 μl of distilled water as described above, the washings collected from the hatched egg shells and stored at −70° C. All of the extract samples were then freeze-dried overnight. The freeze-dried samples were then resuspended in 15 μl of non-reducing SDS sample buffer, centrifuged at 10,000 g for 2 minutes and the entire 15 μl loaded on to 10% gelatine substrate SDS-PAGE gels. Gels were run at 4° C. for 10 minutes at 10 mA followed by a further 25 minutes at 15 mA per gel. They were then incubated for 2×20 minutes in a 2.5% Triton-X 100 solution followed by a three hour incubation in 0.1 M Tris/HCl containing 1 mM $CaCl_2$ pH 8.0. Activity was detected as clear areas on the gel the result of protease activity degrading the gelatine within the gel.

The results from these studies indicated that proteolytic activity was present in a number of different preparations as analyzed using substrate SDSPAGE. Protease activity was detected in the washings obtained from unhatched lice eggs within 12 hours of hatching (FIG. 1, lane 1). This activity was in the higher molecular weight region of the gel. When hair samples that had had lice eggs removed were analyzed on gelatine substrate SDS-PAGE a significant amount of protease activity was detected (FIG. 1, lane 2). The most likely explanation for this activity was that it was of maternal origin being produced at the time of laying. Treatment of hair samples with sodium hypochlorite completely removed the contaminating proteases (FIG. 1, lane 3). In addition treatment of unhatched eggs was also able to remove this protease activity (FIG. 1, lane 4). It was therefore decided to treat all eggs prior to hatching with 1% Na Hypochlorite as described above in order to remove these maternal proteases. Analysis of the washings from freshly hatched egg shells (Egg Shell Washings) indicated the presence of two high molecular weight species (FIG. 1, lane 5). Note only 25 lice eggs were used in this collection, most likely contributing to the lower level of protease activity. These results demonstrate the presence of protease activity directly associated with freshly hatched lice eggs.

In conclusion the hatching process in lice was studied by light microscopy. Egg hatching appears to be associated with physical activity of the developing nymph within the egg. However, the lack of any specialized structures for piercing or loosening the hatch flap or operculum indicates that the hatching process may also involve a biochemical component. While highly active proteases were detected around the time of egg hatching in lice the primary source of these proteases appears to be of maternal origin. Removal of this activity prior to egg hatching was achieved using sodium hypochlorite with the lice progressing through to successfully hatch. Subsequent analysis of the ESW from freshly hatched lice indicated the presence of a limited number of protease species that were further investigated as targets for inhibiting egg hatching in lice.

Example 3

Characterization of Proteases in Egg Shell Washings

In order to evaluate the potential of lice hatching proteases in the egg shell washings as targets for inhibiting egg hatching it was first necessary to characterize the nature of the hatching proteases. Inhibitors of the 4 major classes of proteases were used to classify the proteases in the ESW.

Figure 2:
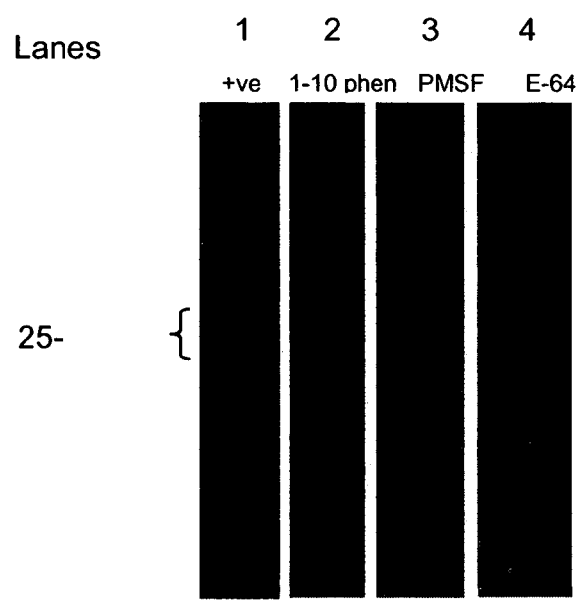
FIG. 2: shows a Coomassie stain of inhibitor treated gelatine SDS-PAGE gels of the egg shell washings from lice eggs following hypochlorite treatment. Three bands were evident at approximately 25-30 kDa (bracketed). Lane 1, ESW positive control no inhibitor treatment, lane 2, ESW after treatment with 10 mM 1,10-phenanthroline, lane 3, ESW after treatment with 5 mM PMSF and lane 4 ESW after treatment with 10 µM E-64. Incubation was performed at 37° C. for 3 hours. Note the significant reduction in protease activity following treatment with 1,10-phenanthroline (lane 2, bracketed region). No reduction in protease activity of the ESW was observed when the aspartic inhibitor pepstatin was used (data not shown).

10% SDS-PAGE gelatine substrate gels were loaded with freeze dried egg shell washings from 100 lice eggs that had been resuspended in 50 μl of non-reducing sample buffer with samples run at 10 μl per lane. Gels were run at 4° C. for 10 minutes at 10 mA per gel followed by a further 25 minutes at 15 mA per gel. Gels were then cut into strips and each strip incubated for 2×20 minutes in a 2.5% Triton-X 100 solution containing a specific inhibitor. The inhibitors used were the serine protease inhibitor PMSF (5 mM), the metalloprotease inhibitor 1,10-phenanthroline (10 mM), the aspartic protease Pepstatin (5 μM) and the cysteine inhibitor E-64 (10 μM). The gel strips were then incubated in 0.1M Tris/HCl containing 1 mM $CaCl_2$ pH 8 containing the different protease inhibitors for 3 hrs at 37° C., before being stained in Coomassie blue and destained as previously described. In contrast to FIG. 1, lane 5 that shows a predominance of proteolytic activity around 25-30 kDa (refer to FIG. 2 brackets). Subsequent analysis of numerous preparations of ESW indicated that this triplet of proteolytic activity around 25-30 kDa was highly reproducible. The results from the inhibitor studies indicate a significant reduction in protease activity following treatment with 1,10-phenanthroline (lane 2 bracketed region). No reduction in protease activity of the ESW was observed when the serine protease inhibitor PMSF or the cysteine protease inhibitor E64 was used. In addition, the aspartic inhibitor pepstatin did not show any reduction in protease activity (data not shown).

Example 4

Development of an In Vitro Bioassay for Measuring Lice Egg Hatching

To evaluate the potential effects of protease inhibitors on lice egg hatching it was necessary to develop a reliable in vitro bioassay. Male and female clothing lice were fed on a rabbit as previously described. Female and male adult lice in a ratio of 3:1 were then transferred to a clean petri dish containing nylon cloth approximately 3×3 $cm^2$ and left for 12 hrs at 32° C. During this period the female lice laid their eggs and attached them to the woven cloth. All lice would then be removed and the eggs permitted to incubate for the following 5 days. On Day 6 the cloth containing the eggs would be placed for 1 minute in a 1% sodium hypochlorite solution and then washed extensively. The eggs would then progress through to their final stages of development and hatch. In untreated control eggs a reliable average percentage hatch of between 85-95 percent was obtained using the in vitro egg hatch assay. It was subsequently found that for the egg hatching assay it was not necessary to pre-treat the lice eggs with sodium hypochlorite.

Example 5

Identification of Compounds that can Inhibit the Activity of Lice Hatching Proteases (a) Testing of Protease Inhibitors Using Lice Egg-Hatching Bioassay.

Having refined a bioassay for measuring egg hatching in lice, the next phase of the research was to use this bioassay as a means of testing the effects of different protease inhibitors on egg hatching.

Lice eggs were laid onto cloth as described above. Five days post laying the cloth containing lice eggs was removed and immersed in a 1% sodium hypochlorite solution before being washed extensively in distilled water and blotted dry on tissue paper. Lice eggs were counted under a dissecting microscope and the cloth cut into batches of between 10-30 eggs with 3-5 replicates used per treatment. The cloth containing lice eggs was then immersed in a protease inhibitor solution for a period of between 2-10 minutes, placed on tissue paper for 1 minute to dry before being transferred to a clean petri dish and incubated until hatching. The eggs were observed at regular time intervals for evidence of eggs hatching over the next 1-2 days by which time the control eggs had hatched. Protease inhibitor solutions were typically prepared as stock solutions and added fresh at the appropriate concentration. Specifically stock solutions were prepared as follows: 1,10-phenanthroline (200 mM in methanol) and Bestatin (5 mg/ml in methanol). In addition, the equivalent levels of the solvent were added to the non-inhibitor containing controls eggs to test for any buffer alone effects. Percentage hatch inhibition was calculated as the percentage reduction in egg hatch compared to the untreated control. The untreated control was assigned a percentage hatch of 100%.

Figure 3:
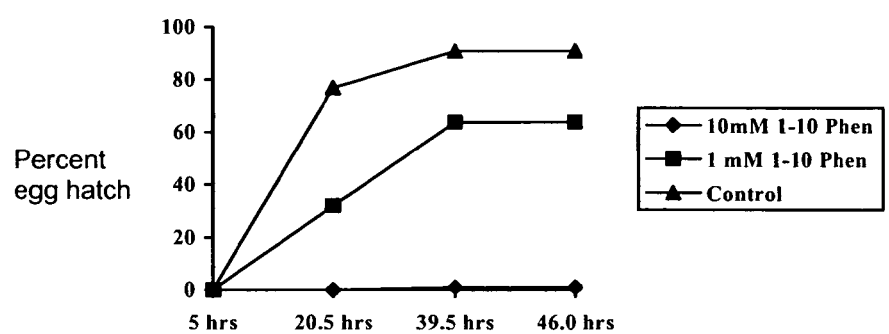
FIG. 3: shows the effect of 1,10-phenanthroline on egg hatching in lice. Eggs were treated 5 days post laying and then hatching observed over time.
Figure 4:
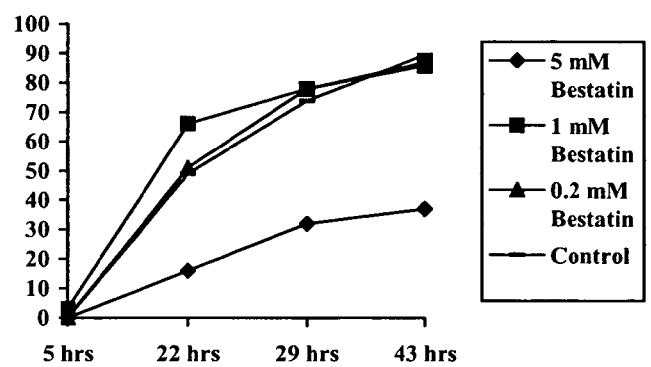
FIG. 4: shows the effect of Bestatin on egg hatching in lice. Eggs 20 were treated 5 days post laying and then hatching observed over time.

The addition of 1,10-phenanthroline, a metal chelating agent and a metalloprotease inhibitor significantly inhibited egg hatching in lice at 10 mM while at 1 mM the level of inhibition was approximately 30% compared to that of the controls (refer to FIG. 3). Bestatin, a metal chelating agent and an inhibitor of metalloproteases and more specifically aminopeptidase M and N, was also able to significantly inhibit lice egg hatching at 5 mM (FIG. 4).

These results provide data on the effect of specific metal chelating agents and metalloprotease inhibitors on egg hatching in lice. It was however noted that when either 1,10-phenanthroline or Bestatin were added within 24 hours of hatching, variable inhibition of egg hatching was observed (data not shown). This variability in hatch inhibition could be due to a number of factors that relate to the specific developmental stage of the louse. Furthermore these studies indicated that it is very difficult to predict the exact time of egg hatch and therefore the choice of a single time point in which to treat the eggs may be problematic when assessing the effects of a specific inhibitor on egg hatch. The in vitro assay system was therefore modified to account for this variability in lice development.

(b) Time Course Experiment Using in the In Vitro Hatching Assay.

A series of time-course experiments was conducted as a means of assessing inhibitors of lice egg hatching. Eggs were laid onto cloth as previously described and then at 24 hr intervals an inhibitor was added to a new group of eggs for eggs up to 120 hrs post laying. The eggs were then incubated at 28° C. for a further 8 days to permit egg hatching. This method of assaying inhibitors more closely mirrors the field situation where lice eggs will be at various stages of development.

The results of these studies are shown in Table 1. Significant inhibition by 1,10-phenanthroline was demonstrated at varying concentrations over the course of lice hatching. A degree of concentration dependence was also observed with the inhibitory effects of 1,10-phenanthroline. The results indicate that time-course experiments provide a more reliable means of assessing the effects of specific inhibitors on lice egg hatching. The addition of Bestatin resulted in significant inhibition, but only when applied approximately 24 hrs prior to egg hatch.

TABLE 1

Percent inhibition of egg hatching following treatment with different concentrations of 1,10-phenanthroline and 5 mM Bestatin at 24 hr intervals post egg laying.

| Inhibitor | Time post egg laying (hr) | | | | | |
|---|---|---|---|---|---|---|
| | 24 hr | 48 hr | 72 hr | 96 hr | 120 hr | 144 hr |
| 10 mM 1,10-phenanthroline | 100 | 100 | 100 | 100 | 100 | 100 |
| 5 mM 1,10-phenanthroline | 100 | 100 | 100 | 100 | 93 | 96 |
| 2.5 mM 1,10-phenanthroline | 100 | 100 | 85 | 85 | 89 | 60 |
| 5 mM Bestatin | — | — | — | — | — | 53 |

Results from the above studies indicate that lice hatching enzymes are proteases of the metallo class as judged by the ability of metal chelating agent and metalloprotease inhibitor 1,10-phenanthroline to inhibit their activity. Furthermore this compound was able to significantly inhibit egg hatching in lice at all time points examined with some evidence of a dose dependent effect particularly when eggs were treated with the lower concentrations around the time of hatching. 1,10-phenanthroline exerts its effects through its ability to chelate metal ions, preferably zinc and thereby inhibiting zinc dependent proteases.

The data for Bestatin also indicated that the compound could partially inhibit lice egg hatching when administered to eggs in the late developmental stage. Bestatin is a cyclic compound comprising an aryl ring substituted with a substituent containing an amine, a hydroxy group, an amide and a carboxylic acid group. Bestatin is an antibiotic of microbial origin, which is used for treating various forms cancer including non lymphocytic leukemia and also different forms of solid tumors including, lung, stomach, bladder, head, neck and oesophagus where it is used under the name of ubenimex. It can be administered with low toxicity to cultured cells, intact animals and humans. While Bestatin is normally used as an inhibitor of purified proteases at micromolar concentrations (10 μM and 130 μM) the data obtained thus far show it being effective at 5 mM. This result may be due to a number of factors including the ability of Bestatin to penetrate the egg and its specificity for the lice hatching proteases.

Example 6

Screening of Protease Inhibitors to Inhibit Lice Egg Hatching

Lice eggs were laid onto cloth as described in Example 4. A series of time-course experiments were set-up as described in Example 5(part (b)). A considerable number of commercially available protease inhibitors/metal chelators were tested in the lice hatching assay to determine the effect of individual protease inhibitors on lice egg hatching (Table 2). Percentage hatch inhibition was calculated as the percentage reduction in egg hatching compared to the untreated control. The untreated control was assigned a percentage hatch of 100%.

TABLE 2

Percentage inhibition of lice egg hatching following treatment with various protease inhibitors. The percentage inhibition refers to the maximum egg hatch inhibition obtained over the time-course of the experiment.

| Number | Inhibitor | % Inhibition* |
|---|---|---|
| 1 | 1-10 phenanthroline (10 mM) | 100 |
| 2 | 2,2-dipyridyl (10 mM) | 100 |
| 3 | 6,6'-Dimethyl-2,2'-dipyridyl (10 mM) | 100 |
| 4 | 5,5'-Dimethyl-2,2'-dipyridyl (10 mM) | 100 |
| 5 | Captopril (23 mM) | 27 |
| 6 | D-L Thiorophan (1 mg/ml) | 20 |
| 7 | Phosphoramidon (5 mM) | 41 |
| 8 | Actinonin (5 mM) | 0 |
| 9 | Bestatin (5 mM) | 58 |
| 10 | NitroBestatin (1 mg/ml) | 0 |
| 11 | Amastatin (5 mM) | 26 |
| 12 | Leuhistin (5 mM) | 0 |
| 13 | Ebelactone (1, 2 and 5 mM) | 0 |
| 14 | L-leucinthiol (5 mM) | 0 |
| 15 | Fumagillin (5 mM) | 0 |
| 16 | Carboxypeptidase inhibitor (5 mM) | 26 |
| 17 | N-CBZ-PRO-LEU-GLY Hydroximate (10 mM) | 0 |
| 18 | Tetracycline (5 mg/ml) | 89 |
| 19 | Doxycycline (5 mg/ml) | 69 |
| 20 | Minocycline (5 mg/ml) | 55 |
| 21 | GM 1489 | 0 |
| 22 | GM 6001 | 0 |
| 23 | Inhibitor IV | 0 |
| 24 | Chlorhexidine dihydrochloride | 0 |

*The percentage inhibition of egg hatching of the different protease inhibitors has been calculated relative to the appropriate controls and represents the maximum egg hatch inhibition observed.

A number of protease inhibitors were shown to markedly inhibit lice egg hatching. The most effective inhibitors tested included metal chelating agents and metalloprotease inhibitors such as 1-10 phenanthroline, 2,2-dipyridyl and 6,6'-Dimethyl-2,2'-dipyridyl, 5,5'-dimethyl-2,2'-dipyridyl (100% inhibition at 10 mM each). Bestatin, a metalloprotease inhibitor was also able to significantly inhibit egg hatching (58% at 5 mM).

Naturally derived matrix metalloprotease (MMP) inhibitors and metal chelating agents that are tetracyclic compounds in which one ring is an aryl ring and wherein the tetracyclic structure is substituted with a number of hydroxy groups, carbonyl groups, an amine and an amide, included: Tetracycline (89% inhibition at 5 mg/ml), Doxycycline (65% inhibition at 5 mg/ml) and Minocycline (55% at 5 mg/ml). These metal chelators showed inhibitory activity towards egg hatching, however the results for these compounds were more variable in magnitude and appeared to be time dependent. The overall usefulness of the hydroxamate inhibitors may be limiting due to the drive to reduce the use of antibiotics in the general environment. These results indicate that MMP inhibitors may also exert an inhibitory effect on lice egg hatching.

Other protease inhibitors that were tested included EDTA at 100 mM, EGTA at 10 mM and Triethanolamine at 5%. The results indicated that these inhibitors did not appear to have an effect on egg hatching at the concentrations used (results not shown).

Example 7

Effect of Washing Eggs Post Treatment with 1-10 Phenanthroline

An experiment was undertaken to determine whether washing of the eggs would effect the inhibitory activity of 1,10-phenanthroline (Table 3). A control group (5% methanol) was also set up. Percentage hatch inhibition was calculated as the percentage reduction in egg hatch compared to the untreated control. The untreated control was assigned a percentage hatch of 100%. The results from this experiment indicate that 1,10-phenanthroline is still highly efficacious at inhibiting lice egg hatching following washing of eggs in water. In later stage eggs that are approaching egg hatch (day 5) the effects appear to reflect a concentration dependence similar to that observed when lower concentrations of the inhibitor were used. It was also noted that a proportion of eggs treated with 1,10-phenanthroline had embryos that appeared to develop normally yet failed to hatch.

TABLE 3

Percent inhibition of egg hatching following treatment with 10 mM 1-10-phenanthroline at 24 hr intervals post egg laying in lice. Lice eggs were treated with inhibitor for 10 minutes and left unwashed or treated and washed for 1 minute and then left to hatch.

| | Time post laying (hr) | | | | |
|---|---|---|---|---|---|
| | 24 hr | 48 hr | 72 hr | 96 hr | 120 hr |
| Treated/not washed | 100 | 100 | 100 | 100 | 100 |
| Treated/was washed | 100 | 100 | 100 | 97 | 62 |

Example 8

Inhibition of Hatching of Head Lice Eggs with 1-10 Phenanthroline

Tests were carried out to determine if metal chelating agent and metalloprotease inhibitor 1,10-phenanthroline could inhibit head lice egg (Pediculus humanus capitus) hatching as opposed to body lice. Head lice eggs were obtained by placing groups of both 1-2 adult male and 6-8 adult female head lice in separate wells in a 24 well petri dish containing cotton cloth. The petri dish was transferred to a humid incubator at 32° C., 70% RH for 12 hours to permit the female lice to lay their eggs. After 12 hours, all adult lice were removed from the petri dish wells and a series of time-course experiments conducted. A group of eggs (24 hr old) was treated for 10 minutes with 200 µl of a 10 mM solution of 1,10-phenanthroline. A control (i.e., no inhibitor treatment) group of eggs was also included. The eggs were removed from the inhibitor, blotted dry on tissue paper, placed at 32° C., 70% RH and left to hatch. A second group of eggs, (48 hr old) were treated as previously described and also left to hatch. This process was repeated at 24 hr intervals on head lice eggs up to 120 hr post laying. This method of assaying inhibitors more closely mirrors the field situation where lice eggs will be at various stages of development on the head and permits the inhibitory effects to be observed on these different stages of the parasite.

The results from the above studies indicate that 1,10-phenanthroline can significantly inhibit egg hatching in head lice (Table 4).

TABLE 4

Percent inhibition of egg hatching following treatment with 10 mM 1,10-phenanthroline at 24 hr intervals post egg laying in lice relative to the control.

| | Days post laying | | | | |
|---|---|---|---|---|---|
| | 1 | 2 | 3 | 4 | 5 |
| Treated | 100 | 87 | 88 | 100 | 100 |

These results strongly suggest that body lice are an effective model for assaying the effects of protease inhibitors in egg hatching of head lice.

Example 9

Inhibition of Lice Egg Hatching with Metal Chelators

Experiments were conducted using two metal chelating agents that can act as metalloprotease inhibitors to determine their effects on lice egg hatching. These compounds were tested in the standard lice assay to determine their ovicidal effects (refer to example 5 and 6 on methods used to test inhibitors). The following metal chelating agents were evaluated: 2,2'-dipyridyl and 6,6'-Dimethyl-2,2'-dipyridyl. The results of this study are shown in Tables 5 and 6.

TABLE 5

Results of egg hatching following treatment with 2,2'-dipyridyl at 24 hr intervals post egg laying. The results are indicated for: N (number of eggs per replicate), H (number of eggs successfully hatched) and Ph (number of eggs partly hatched).

| | 24 hr | | | 48 hr | | | 72 hr | | | 96 hr | | | 120 hr | | |
|---|---|---|---|---|---|---|---|---|---|---|---|---|---|---|---|
| Replicates | N | H | Ph | N | H | Ph | N | H | Ph | N | H | Ph | N | H | Ph |
| 1 | 7 | 0 | 0 | 6 | 0 | 0 | 7 | 0 | 0 | 13 | 0 | 0 | 10 | 0 | 0 |
| 2 | 8 | 0 | 0 | 14 | 0 | 0 | 7 | 0 | 0 | 9 | 1 | 0 | 10 | 0 | 0 |
| 3 | 11 | 0 | 0 | — | — | — | 14 | 0 | 0 | 10 | 0 | 0 | 13 | 0 | 0 |

TABLE 6

Results of egg hatching following treatment with 6,6'-Dimethyl-2,2'-dipyridyl at 24 hr intervals post egg laying. The results are indicated for: N (number of eggs per replicate), H (number of eggs successfully hatched) and Ph (number of eggs partly hatched).

| | 24 hr | | | 48 hr | | | 72 hr | | | 96 hr | | | 120 hr | | |
|---|---|---|---|---|---|---|---|---|---|---|---|---|---|---|---|
| Replicates | N | H | Ph | N | H | Ph | N | H | Ph | N | H | Ph | N | H | Ph |
| 1 | 10 | 0 | | 13 | 0 | 0 | 15 | 0 | 0 | 25 | 0 | 0 | 23 | 0 | 0 |
| 2 | 10 | 0 | 0 | 11 | 0 | 0 | 16 | 0 | 0 | 22 | 0 | 0 | 9 | 0 | 0 |
| 3 | 11 | 0 | 0 | 6 | 0 | 0 | 10 | 0 | 0 | 18 | 0 | 0 | — | — | — |

The results from these studies indicate that both 6,6'-Dimethyl-2,2'-dipyridyl and 2,2'-dipyridyl displayed very strong ovicidal activity whereby lice egg hatching was completely inhibited at all time points examined. Both 6,6'-Dimethyl-2,2'-dipyridyl and 2,2'-dipyridyl are metal chelating agents and metalloprotease inhibitors that are non-intercalating.

Example 10

Comparative Assessment of Commercial Lice Products with 1,10-Phenanthroline

The ovicidal properties of three major commercial head lice products were evaluated in the standard lice egg-hatching assay. The 3 commercial head lice products were as follows:
1. KP-24® Nelson Laboratories, active ingredients 1% maldison (malathion);
2. RID® Bayer, active ingredients, 1% pyrethrins; and
3. NIX® Pfizer, active ingredients, 1% permethrin.

These three products were tested according to manufacturer's recommendations. Groups of eggs (24 hr old) were treated with the different products according to manufacturer's recommendations for the appropriate period of time (5-10 minutes) followed by a rinse for 1-2 minutes in 32° C. water. A positive controls (10 mM 1,10-phenanthroline) and two negative controls (no treatment and 20% Methanol) were also incorporated. Post exposure to the different products, the eggs were rinsed with warm water at 32° C. before being blotted dry on tissue paper and placed at 32° C., 70% RH and left to hatch. A second group of eggs, (48 hr old) were treated as previously described and also left to hatch. This process was repeated at 24 hr intervals on head lice eggs up to 120 hr post laying. This method of assaying inhibitors more closely mirrors the field situation where lice eggs will be at various stages of development on the head and permits the inhibitory effects to be observed on these different stages of the parasite. The results of these studies are shown in Table 7.

TABLE 7

Results of egg hatching following treatment with 3 commercial head lice products, 10 mM 1,10-phenanthroline and controls at 24 hr intervals post egg laying. The results are indicated for: N (number of eggs per replicate), H (number of eggs successfully hatched) and Ph (number of eggs partly hatched).

| Replicates | 24 hr | | | 48 hr | | | 72 hr | | | 96 hr | | | 120 hr | | |
|---|---|---|---|---|---|---|---|---|---|---|---|---|---|---|---|
| | N | H | Ph | N | H | Ph | N | H | Ph | N | H | Ph | N | H | Ph |
| NIX-Pfizer | | | | | | | | | | | | | | | |
| 1 | 16 | 12 | 2 | 9 | 7 | 0 | 18 | 3 | 3 | 12 | 8 | 3 | 19 | 12 | 3 |
| 2 | 10 | 4 | 3 | 6 | 2 | 3 | 10 | 3 | 3 | 15 | 7 | 5 | 18 | 8 | 7 |
| 3 | 10 | 7 | 2 | 9 | 4 | 3 | 17 | 5 | 7 | — | — | — | 36 | 21 | 5 |
| RID-Bayer | | | | | | | | | | | | | | | |
| 1 | 8 | 0 | 3 | 12 | 3 | 4 | 7 | 0 | 0 | 8 | 0 | 0 | 14 | 0 | 1 |
| 2 | 8 | 2 | 5 | 7 | 0 | 1 | 5 | 1 | 2 | 8 | 0 | 0 | — | — | — |
| 3 | 5 | 0 | 2 | 10 | 0 | 2 | 6 | 1 | 3 | 11 | 0 | 0 | — | — | — |
| KP24KP24 | | | | | | | | | | | | | | | |
| 1 | 7 | 7 | 0 | 10 | 10 | 0 | 10 | 1 | 3 | 10 | 0 | 0 | 10 | 0 | 0 |
| 2 | 6 | 6 | 0 | 10 | 9 | 0 | 0 | 0 | 0 | 7 | 0 | 0 | 8 | 0 | 0 |
| 3 | 9 | 8 | 0 | — | — | — | — | — | — | — | — | — | 12 | 0 | 1 |
| 1,10-phenanthroline (10 mM) | | | | | | | | | | | | | | | |
| 1 | 13 | 0 | 0 | 5 | 0 | 0 | 7 | 0 | 0 | 10 | 0 | 0 | 9 | 0 | 0 |
| 2 | 9 | 0 | 0 | 15 | 0 | 0 | 7 | 0 | 0 | 10 | 0 | 0 | 6 | 4 | 0 |
| 3 | — | — | — | 8 | 0 | 0 | 9 | 0 | 0 | — | — | — | 7 | 1 | 0 |
| Control (20% Methanol) | | | | | | | | | | | | | | | |
| 1 | — | — | — | 14 | 14 | 0 | 10 | 10 | 0 | 10 | 10 | 0 | 13 | 13 | 0 |
| 2 | — | — | — | 5 | 4 | 0 | 8 | 8 | 0 | 10 | 9 | 0 | 7 | 7 | 0 |
| 3 | — | — | — | — | — | — | 0 | 9 | 7 | 0 | 4 | 4 | 0 | 10 | 10 | 0 |
| Control (Untreated) | | | | | | | | | | | | | | | |
| 1 | 10 | 9 | 0 | 11 | 11 | 0 | 25 | 24 | 0 | 10 | 8 | 0 | 20 | 20 | 0 |
| 2 | 20 | 18 | 0 | 8 | 7 | 0 | 10 | 10 | 0 | 11 | 10 | 0 | 20 | 18 | 0 |
| 3 | — | — | — | 8 | 8 | 0 | — | — | — | 10 | 10 | 0 | — | — | — |

Results from the testing of 3 commercial pediculicides indicate that they displayed inconsistent levels of ovicidal activity across the different stages of lice egg hatching. Whereas, the compound 1,10-phenanthroline was highly effective at inhibiting lice egg hatching.

Example 11

Assessment of Additional Commercial Lice Products

The ovicidal properties of two major commercial head lice products were evaluated in the standard lice egg-hatching assay. The 2 commercial head lice products were as follows:
1. Pronto Plus® Shampoo Del Laboratories, active ingredients 0.33% Pyrethrins; and
2. Pronto Plus® Mousse Shampoo Del Laboratories, active ingredients, 0.33% Pyrethrins.

These two products were tested according to manufacturer's recommendations. Groups of eggs (24 hr old) were treated with the different products according to manufacturer's recommendations for the appropriate period of time (5-10 minutes) followed by a rinse for 1-2 minutes in 32° C. water. Two negative controls (no treatment and 20% ethanol) were also incorporated. Post exposure to the different products, the eggs were blotted dry on tissue paper and placed at 32° C., 70% RH and left to hatch. A second group of eggs, (48 hr old) were treated as previously described and also left to hatch. This process was repeated at 24 hr intervals on head lice eggs up to 120 hr post laying. This method of assaying inhibitors more closely mirrors the field situation where lice eggs will be at various stages of development on the head and permits the inhibitory effects to be observed on these different stages of the parasite. The results of these studies are shown in Table 8.

TABLE 8

Results of egg hatching following treatment with 2 commercial head lice products and controls at 24 hr intervals post egg laying. The results are indicated for: N (number of eggs per replicate), H (number of eggs successfully hatched) and Ph (number of eggs partly hatched).

| Replicates | 24 hr | | | 48 hr | | | 72 hr | | | 96 hr | | | 120 hr | | |
|---|---|---|---|---|---|---|---|---|---|---|---|---|---|---|---|
| | N | H | Ph | N | H | Ph | N | H | Ph | N | H | Ph | N | H | Ph |
| Pronto Plus Shampoo | | | | | | | | | | | | | | | |
| 1 | 14 | 10 | 2 | 11 | 9 | 0 | 30 | 27 | 0 | 35 | 30 | 0 | 40 | 38 | 2 |
| 2 | 20 | 15 | 3 | 21 | 18 | 0 | 19 | 16 | 0 | 42 | 36 | 0 | 38 | 29 | 5 |
| 3 | — | — | — | — | — | — | — | — | — | — | — | — | — | — | — |

TABLE 8-continued

Results of egg hatching following treatment with 2 commercial head lice
products and controls at 24 hr intervals post egg laying. The results are indicated for:
N (number of eggs per replicate), H (number of eggs successfully hatched) and Ph
(number of eggs partly hatched).

| Replicates | 24 hr | | | 48 hr | | | 72 hr | | | 96 hr | | | 120 hr | | |
|---|---|---|---|---|---|---|---|---|---|---|---|---|---|---|---|
| | N | H | Ph | N | H | Ph | N | H | Ph | N | H | Ph | N | H | Ph |
| Pronto Plus Mousse Shampoo | | | | | | | | | | | | | | | |
| 1 | 10 | 8 | 0 | 18 | 15 | 0 | 47 | 31 | 9 | 63 | 8 | 34 | 51 | 7 | 40 |
| 2 | 15 | 13 | 0 | 10 | 6 | 0 | 30 | 14 | 8 | 29 | 5 | 10 | 50 | 8 | 30 |
| 3 | 11 | 9 | 0 | — | — | — | 34 | 13 | 17 | 21 | 1 | 15 | 31 | 1 | 17 |
| Control (ethanol) | | | | | | | | | | | | | | | |
| 1 | 12 | 10 | 0 | 18 | 16 | 0 | 40 | 36 | 1 | 21 | 20 | 0 | 49 | 47 | 0 |
| 2 | 11 | 9 | 0 | 21 | 18 | 0 | 41 | 37 | 0 | 28 | 26 | 0 | 39 | 36 | 0 |
| 3 | 11 | 11 | 0 | 13 | 11 | 0 | 75 | 70 | 0 | 29 | 27 | 0 | 36 | 34 | 0 |
| Control (untreated) | | | | | | | | | | | | | | | |
| 1 | 10 | 9 | 0 | 27 | 26 | 0 | 61 | 60 | 0 | 50 | 49 | 1 | 48 | 46 | 0 |
| 2 | — | — | — | — | — | — | — | — | — | — | — | — | — | — | — |
| 3 | — | — | — | — | — | — | — | — | — | — | — | — | — | — | — |

Results from the testing of 2 commercial pediculicides indicate that they displayed very poor and inconsistent ovicidal activity across the different stages of lice egg hatching.

Example 12

Evaluation of Compounds on Egg Hatching of *Plutella xylostella*

Several hundred *Plutella xylostella* eggs (Waite strain) were collected, that had been laid over a 24 hour period. Within 3-5 hours of collection, the eggs were treated with different inhibitors as described below.

Batches of *Plutella* eggs that had been laid on either fine cloth or parafilm were dipped in a specific inhibitor solution for between 2-10 seconds, the excess solution was drained by blotting with dry tissue paper. The egg masses were then placed in a humid box at 25 degrees until egg hatch. Control eggs were exposed to absolute methanol as described above. At day 6 post laying the eggs were assessed from the different treatments and the percentage of egg hatch determined relative to the control as shown in Table 9.

TABLE 9

Ovicidal effects of inhibitors on egg hatch of *Plutella xylostella* relative to control.

| Inhibitor | Number hatched | Number unhatched | % Inhibition |
|---|---|---|---|
| 6,6'-dimethyl-2,2'-dipyridyl (10 mM) | 0 | 79 | 100 |
| 6,6'-dimethyl-2,2'-dipyridyl (1 mM) | 0 | 26 | 100 |
| 6,6'-dimethyl-2,2'-dipyridyl (0.1 mM) | 23 | 29 | 0 |
| 6,6'-dimethyl-2,2'-dipyridyl (0.01 mM) | 13 | 7 | 0 |
| 6,6'-dimethyl-2,2'-dipyridyl (0.001 mM) | 11 | 6 | 0 |
| 1,10-phenanthroline (10 mM) | 0 | 45 | 100 |
| 1,10-phenanthroline (1 mM) | 15 | 16 | 0 |
| Control (100% MeOH) | 63 | 92 | — |

Table 9 indicates that the metal chelator 6,6'-dimethyl-2,2'dipyridyl was able to inhibit egg hatching in *Plutella xylostella* in a dose dependent manner, with strong ovicidal effects evident at both 10 and 1 mM. In addition, the metalloprotease inhibitor/metal chelator, 1,10-phenanthroline was also able to significantly inhibit egg hatching of this insect at 10 mM.

Example 13

Evaluation of Compounds on Egg Hatching of *Plutella xylostella*

Several hundred *Plutella xylostella* eggs (Waite strain) were collected, that had been laid over a 24 hour period. Within 3-5 hours of collection, all of the eggs were treated with different inhibitors as described below.

Batches of *Plutella* eggs that were laid on either fine cloth or parafilm were dipped in a specific inhibitor solution for between 2-10 seconds, the excess solution was drained by blotting with dry tissue paper. The egg masses were then placed in a humid box at 25 degrees until egg hatch. Control eggs were exposed to absolute methanol as described above or not treated. At day 6 post laying the eggs were assessed from the different treatments and the percentage of egg hatch determined relative to the controls as shown in Tables 10 and 11.

TABLE 10

Ovicidal effects of inhibitors on egg hatch of *Plutella xylostella* relative to controls (eggs laid on cloth).

| Inhibitor | Number hatched | Number unhatched | % Inhibition |
|---|---|---|---|
| 6,6'-dimethyl-2,2'-dipyridyl (10 mM) | 0 | 53 | 100 |
| 6,6'-dimethyl-2,2'-dipyridyl (1 mM) | 0 | 23 | 100 |
| 6,6'-dimethyl-2,2'-dipyridyl (0.1 mM) | 49 | 49 | 0 |
| 6,6'-dimethyl-2,2'-dipyridyl (0.01 mM) | 23 | 4 | 12 |
| 5,5'-dimethyl-2,2'-dipyridyl (10 mM) | 0 | 21 | 100 |
| 5,5'-dimethyl-2,2'-dipyridyl (1 mM) | 5 | 22 | 78 |
| 4,4'-dimethyl-2,2'-dipyridyl (10 mM) | 0 | 36 | 100 |
| 4,4'-dimethyl-2,2'-dipyridyl (1 mM) | 0 | 30 | 100 |
| Control (untreated) | 32 | 1 | — |
| Control (100% MeOH) | 34 | 1 | — |

TABLE 11

Ovicidal effects of inhibitors on egg hatch of *Plutella xylostella* relative to controls (eggs laid on parafilm).

| Inhibitor | Number hatched | Number unhatched | % Inhibition |
|---|---|---|---|
| 6,6'-dimethyl-2,2'-dipyridyl (10 mM) | 0 | 106 | 100 |
| 6,6'-dimethyl-2,2'-dipyridyl (1 mM) | 0 | 63 | 100 |
| 6,6'-dimethyl-2,2'-dipyridyl (0.1 mM) | 65 | 70 | 7 |
| 6,6'-dimethyl-2,2'-dipyridyl (0.01 mM) | 92 | 4 | 0 |
| 5,5'-dimethyl-2,2'-dipyridyl (10 mM) | 0 | 142 | 100 |
| 5,5'-dimethyl-2,2'-dipyridyl (1 mM) | 18 | 151 | 88 |
| 4,4'-dimethyl-2,2'-dipyridyl (10 mM) | 0 | 139 | 100 |
| 4,4'-dimethyl-2,2'-dipyridyl (1 mM) | 10 | 121 | 91 |
| Control (untreated) | 108 | 3 | — |
| Control (100% MeOH) | 58 | 7 | — |

Tables 10 and 11 show the effects of exposing *Plutella xylostella* eggs to selected dipyridyl compounds on egg hatching relative to controls. The results show a dose dependent effect for 6,6'-dimethyl-2,2'dipyridyl with both 10 and 1 mM being effective at inhibiting egg hatching of the *Plutella* eggs. At 0.1 and 0.01 mM, there was no observable effects on egg hatching. These results confirm the results shown in Example 12 for this compound. In addition, both 5,5'-dimethyl-2,2'dipyridyl and 4,4'-dimethyl-2,2'dipyridyl were able to significantly inhibit egg hatching at both 10 and 1 mM.

There were no significant differences observed between eggs laid on either cloth or parafilm.

Example 14

Evaluation of Compounds on Egg Hatching of *Helicoverpa armigera*

Several hundred *Helicoverpa armigera* eggs (Tatura x Toowoomba strains) were collected, that had been laid on fine mesh cloth over a 24 hour period. Within 3-5 hours of collection, all of the eggs were treated with different inhibitors as described below.

Batches of *Helicoverpa* eggs were exposed to a specific inhibitor solution for between 2-10 seconds the excess solution drained by blotting with dry tissue paper. The egg masses were then placed in a humid box at 25 degrees until egg hatch. Control eggs were exposed to absolute methanol as described above. At day 6 post laying the eggs were assessed from the different treatments and the percentage of egg hatch determined relative to the control as shown in Table 12.

TABLE 12

Ovicidal effects of inhibitors on egg hatch of *Helcoverpa armigera* eggs relative to control.

| Inhibitor | Number hatched | Number unhatched | % Inhibition |
|---|---|---|---|
| 6,6'-dimethyl-2,2'-dipyridyl (10 mM) | 7 | 98 | 94 |
| 6,6'-dimethyl-2,2'-dipyridyl (1 mM) | 4 | 140 | 97 |
| 6,6'-dimethyl-2,2'-dipyridyl (0.1 mM) | na | na | 0 |
| 6,6'-dimethyl-2,2'-dipyridyl (0.01 mM) | na | na | 0 |
| 6,6'-dimethyl-2,2'-dipyridyl (0.001 mM) | na | na | 0 |
| 1,10-phenantholine (10 mM) | 31 | 16 | 44 |
| 1,10-phenantholine (1 mM) | na | na | 0 |
| Control (100% MeOH) | na | na | 0 | na refers to all of the eggs hatching and being devoured by the newly hatched caterpillars.

The results in Table 12 indicate that 6,6'-dimethyl-2,2'dipyridyl was able to significantly inhibit egg hatching of *Helcoverpa armigera* eggs at 10 and 1 mM. No inhibition was recorded at concentrations below this level. The compound 1,10-phenanthroline was also able to inhibit egg hatching at 10Mm only.

Example 15

Evaluation of Compounds on Egg Hatching of *Helicoverpa armigera*

Several hundred *Helicoverpa armigera* eggs (Tatura x Toowoomba strains) were collected, that had been laid on fine mesh cloth over a 24 hour period. Within 3-5 hours of collection, all of the eggs were treated with different inhibitors as described below.

Batches of *Helicoverpa* eggs were then exposed to a specific inhibitor solution for between 2-10 seconds the excess solution drained by blotting with dry tissue paper. The egg masses were then placed in a humid box at 25 degrees until egg hatch. Control eggs were exposed to absolute methanol as described above. At day 6 post laying the eggs were assessed from the different treatments and the percentage of egg hatch determined relative to the control as shown in Table 13.

TABLE 13

Ovicidal effects of inhibitors on egg hatch of *Helicoverpa armigera* relative to the control.

| Inhibitor | Number hatched | Number unhatched | % Inhibition |
|---|---|---|---|
| 6,6'-dimethyl-2,2'-dipyridyl (10 mM) | 3 | 48 | 94 |
| 6,6'-dimethyl-2,2'-dipyridyl (1 mM) | 2 | 61 | 97 |
| 6,6'-dimethyl-2,2'-dipyridyl (0.1 mM) | 70 | 0 | 0 |
| 5,5'-dimethyl-2,2'-dipyridyl (10 mM) | 0 | 42 | 100 |
| 4,4'-dimethyl-2,2'-dipyridyl (10 mM) | 8 | 43 | 84 |
| 4,4'-dimethyl-2,2'-dipyridyl (1 mM) | 23 | 29 | 66 |
| Control (100% MeOH) | 37 | 2 | — |

The data presented in Table 13, support the previous results provided in Example 4 demonstrating that 6,6'-dimethyl-2,2'-dipyridyl is able to significantly inhibit the egg hatching of *Helicoverpa armigera* eggs at both 10 and 1 mM. At 0.1 mM, no inhibition of egg hatching was observed with this compound. In addition, data is presented that indicates significant inhibition of egg hatching at 10 mM for both 5,5'-dimethyl-2,2'-dipyridyl and 4,4'-dimethyl-2,2'-dipyridyl. In addition, significant inhibition of egg hatching was observed at 1 mM 4,4'-dimethyl-2,2'-dipyridyl.

Example 16

Evaluation of Effects of 2-(2-Pyridinyl)Quinone on Hatching of *Plutella xylostella* Eggs Several hundred *Plutella xylostella* eggs (Waite strain) were collected, that had been laid over a 24 hour period. Within 24-48 hours of collection, the eggs were treated with different inhibitors as described below.

Batches of *Plutella* eggs that had been laid on fine cloth were dipped in a specific inhibitor solution for approximately 2 seconds, the excess solution was drained by blotting with dry tissue paper. The egg masses were then placed in a humid box at 25 degrees until egg hatch. Control eggs were exposed to absolute ethanol as described above. On day 6 post laying the eggs were assessed from the different treatments and the percentage of egg hatch determined relative to the control.

Results:

TABLE 14

Ovicidal effects of inhibitors on egg hatch of *Plutella xylostella* relative to control.

| Inhibitor | Number hatched | Number unhatched | % Inhibition |
|---|---|---|---|
| 2-(2-pyridinyl)quinoline (10 mM) | 2 | 56 | 96 |
| Control (100% ETOH) | 55 | 14 | — |

Table 14 indicates that the metal chelating compound 2-(2-pyridinyl)quinoline was able to inhibit egg hatching in *Plutella xylostella* at 10 mM.

Example 17

Evaluation of Effects of Added Metal Ions on Inhibition of Egg Hatching by 6,6'-Dimethyl-2,2'-Dipyridyl Several hundred *Plutella xylostella* eggs (Waite strain) were collected, that had been laid over a 24 hour period. Within 24 hours of collection the following experimental design was chosen. Batches of eggs were exposed to 10 mM 6,6'-dimethyl-2,2'-dipyridyl for 2 seconds while additional batches of eggs were exposed to the solvent only (Methanol) for 2 seconds. All batches of eggs were allowed to air dry for 20 minutes at room temperature. The eggs were then given a 2 second exposure to $FeSO_4$ at either 10, 5 or 1 mM, air dried and put in the incubator at 24° C. and allowed to hatch over the next 6 days. In addition, a positive control of 10 mM 6,6'-dimethyl-2,2'-dipyridyl was set up in which eggs were exposed to this compound for 2 seconds, air dried and placed in the incubator.

Results

TABLE 15

Reversal of the ovicidal effects of 10 mM 6,6'-dimethyl-2,2'-dipyridyl on egg hatch of *Plutella xylostella* relative to the $FeSO_4$ controls.

| Inhibitor | Number hatched | Number unhatched | % Inhibition |
|---|---|---|---|
| 6,6'-dimethyl-2,2'-dipyridyl (+ve) control | 0 | 44 | 100 |
| 6,6'-dimethyl-2,2'-dipyridyl followed by 2 second exposure to MEOH | 3 | 28 | 90 |
| 6,6'-dimethyl-2,2'-dipyridyl followed by 2 second exposure to 10 mM $FeSO_4$ | 12 | 19 | 38 |
| 6,6'-dimethyl-2,2'-dipyridyl followed by 2 second exposure to 5 mM $FeSO_4$ | 25 | 0 | 0 |
| 6,6'-dimethyl-2,2'-dipyridyl followed by 2 second exposure to 1 mM $FeSO_4$ | 33 | 1 | 3 |

Results presented in Table 15 indicate that the addition of the divalent metal ions in the form of Fe in $FeSO_4$ was able to reverse the effects of the metal chelating agent 6,6'-dimethyl-2,2'-dipyridyl. The results indicate that the reversal of the inhibitory effects of 6,6'-dimethyl-2,2'-dipyridyl are due to Fe replacing the action of this inhibitor as opposed to a simple dilution of the inhibitor by the $FeSO_4$. This effect is indicated by the finding that exposure of the eggs to MeOH alone post exposure to the inhibitor still resulted in a significant degree of inhibition of egg hatching.

Example 18

Evaluation of Effects of Added Metal Ions on Inhibition of Egg Hatching by 5,5'-Dimethyl-2,2'-Dipyridyl Several hundred *Plutella xylostella* eggs (Waite strain) were collected, that had been laid over a 24 hour period. Within 24 hours of collection the following experimental design was chosen. Batches of eggs were exposed to 10 mM 5,5'-dimethyl-2,2'-dipyridyl for 2 seconds while additional batches of eggs were exposed to the solvent only (Methanol) for 2 seconds. All batches of eggs were allowed to air dry for 20 minutes at room temperature. The eggs were then given a 2 second exposure to $FeSO_4$ at 10, 5 or 1 mM, air dried and put in an incubator at 24° C. and allowed to hatch over the next 6 days. In addition, a positive control of 10 mM, 5,5'-dimethyl-2,2'-dipyridyl was set us in which eggs were exposed to this compound for 2 seconds, air dried and placed in the incubator.

Results

TABLE 16

Reversal of the ovicidal effects of 10 mM 5,5'-dimethyl-2,2'-dipyridyl on egg hatch of *Plutella xylostella* relative to the $FeSO^4$ only controls.

| Inhibitor | Number hatched | Number unhatched | % Inhibition |
|---|---|---|---|
| 5,5'-dimethyl-2,2'-dipyridyl (+ve) control | 0 | 38 | 100 |
| 5,5'-dimethyl-2,2'-dipyridyl followed by 2 second exposure to MEOH | 16 | 19 | 55 |
| 5,5'-dimethyl-2,2'-dipyridyl followed by 2 second exposure to 10 mM $FeSO_4$ | 23 | 2 | 8 |
| 5,5'-dimethyl-2,2'-dipyridyl followed by 2 second exposure to 5 mM $FeSO_4$ | 25 | 0 | 0 |
| 5,5'-dimethyl-2,2'-dipyridyl followed by 2 second exposure to 1 mM $FeSO_4$ | 39 | 1 | 3 |

Results presented in Table 16 indicate that the addition of the divalent metal ions in the form of Fe in $FeSO_4$ was able to reverse the effects of the metal chelating agent 5,5'-dimethyl-2,2'-dipyridyl. The results indicate that the reversal of the inhibitory effects of 5,5'-dimethyl-2,2'-dipyridyl are due to Fe removing the action of this inhibitor as opposed to a simple dilution of the inhibitor by the $FeSO_4$. This effect is indicated by the finding that exposure of the eggs to MeOH alone post exposure to the inhibitor still resulted in a significant degree of inhibition of egg hatching.

Example 19

Effects of 6,6'-Dimethyl-2,2'-Dipyridyl and 5,5'-Dimethyl-2,2'-Dipyridyl on Egg Hatching in *Bovicola Ovis*

*B. ovis* eggs were collected from the wool of sheep that were infested with this parasite. The eggs were collected using forceps and with the aid of a dissecting microscope and placed in 24 well tissue culture plates in duplicate lots of 10 eggs per replicate. The eggs were then exposed to either methanol alone (control) or the test compounds for either 10 minutes or 1 minute before being removed from the wells and placed into individual glass vials containing a diet at the base of the tube. The tubes were placed in plastic containers containing a salt solution (to keep humidity constant at 68%) and the containers maintained at a temperature 32° C. The eggs were monitored for hatching over the following 12 days and % hatch inhibition determined in comparison to the controls.

TABLE 17

Effects of 6,6'-dimethyl-2,2'-dipyridyl and 5,5'-dimethyl-2,2'-dipyridyl on egg hatching in Bovicola ovis.

| Inhibitor | Number hatched in different replicates | Number unhatched | % Inhibition |
|---|---|---|---|
| 10 mM 5,5'-dimethyl-2,2'-dipyridyl (10 minute exposure) | Rep 1. 0<br>Rep 2. 0 | 10<br>10 | 100 |
| 10 mM 5,5'-dimethyl-2,2'-dipyridyl (1 minute exposure) | Rep 1. 0<br>Rep 2. 0 | 10<br>10 | 100 |
| 10 mM 6,6'-dimethyl-2,2'-dipyridyl (10 minute exposure) | Rep 1. 0<br>Rep 2. 0 | 10<br>10 | 100 |
| 10 mM 6,6'-dimethyl-2,2'-dipyridyl (1 minute exposure) | Rep 1. 0<br>Rep 2. 0 | 10<br>10 | 100 |
| Control (Ethanol) (10 minute exposure) | Rep 1. 5<br>Rep 2. 5 | 5<br>5 | — |
| Control (Ethanol) (1 minute exposure) | Rep 1. 4<br>Rep 2. 5 | 6<br>5 | — |
| Control (Untreated) | Rep 1. 3<br>Rep 2. 6 | 7<br>3 | — |

The results presented in Table 17 indicate that following a 10 or a 1 minute exposure of B. bovis louse eggs to a 10 mM solution of either 5,5 '-dimethyl-2,2'-dipyridyl or 6,6'-dimethyl-2,2'-dipyridyl that egg hatching in this ectoparasite could be completely inhibited in this assay.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed above are incorporated herein in their entirety.

Any discussion of documents, acts, materials, devices, articles or the like which was included in the present specification is solely for the purpose of 5 providing a context for the present invention. It is not to be taken as an admission that any or all of these matters form part of the prior art base or were common general knowledge in the field relevant to the present invention as it existed in any country before the priority date of each claim of this application.

REFERENCES

Al-Sayah, M. H., McDonald, R., Branda, N. R., *Euro. J. Org. Chem.*, 2004, 173-182.

Buhleier, E., Wehner, W., Vogthe, F., *Chem. Ber.*, 1978, 111, 200-5 204.

Busvine, J. R., Entomology and evolution. *Antenna.* 1993,17: 196-201.

Busvine, J. R, Biology of the parasites. *Cutaneous Infestations and Insect Bites* (M. Orkin and H. I. Maibach, eds) .1985, pp. 163-174. New York: Marcel Dekker.

Dymock, J. J., Laing W. A., Shaw B. D., Gatehouse A. M. R, Cristellar. J. T. *New Zealand Journal of Zoology,* 1992, 19: 123-131.

Green, T. W. and Wutz, P., *Protecting groups of organic synthesis*, John Wiley & Son, $3^{rd}$ Edition, 1999.

Imperiali, B. and Fisher, S. L., *J. Org. Chem.*, 1992, 57, 757-759.

Jones, J., *Amino acid synthesis and peptide synthesis*, Oxford Chemistry Press, 1992.

Samuels R. I. and Paterson J. C. *Comparative Biochemistry and Physiology.* 1995 110B: 661-669.

The claims defining the invention are as follows:

The claims defining the invention are as follows:

1. A composition comprising 5,5'-dimethyl-2,2'-dipyridyl, or a pharmaceutically, veterinary, or agriculturally acceptable salt thereof, wherein the composition is formulated for topical application and in a form selected from the group consisting of a dip, spray, aerosol, shampoo, mousse, emulsion, foam, cream, dust, gel, and lotion.

2. The composition of claim 1, wherein the composition is formulated for application to skin.

3. The composition of claim 2, wherein the composition is formulated for application to the human scalp.

4. The composition of claim 1, wherein the composition is formulated for use in a direct topical application in a form of a shampoo or lotion.

5. The composition of claim 1, wherein 5,5'-dimethyl-2,2'-dipyridyl is present at a concentration between 0.0001 mM and 1 M.

6. The composition of claim 1, wherein 5,5'-dimethyl-2,2'-dipyridyl is present at a concentration between 0.01 mM and 100 mM.

7. The composition of claim 1, wherein 5,5'-dimethyl-2,2'-dipyridyl is present at a concentration between 0.1 mM and 30 mM.

8. The composition of claim 1, wherein 5,5'-dimethyl-2,2'-dipyridyl is present at a concentration between 5 mM and 15 mM.

9. A composition comprising
   (i) 5,5'-dimethyl-2,2'-dipyridyl, or a pharmaceutically, veterinary or agriculturally acceptable salt thereof;
   and (ii) a second ectoparasiticide;
   wherein the composition is formulated for topical application and in a form selected from the group consisting of a dip, spray, aerosol, shampoo, mousse, emulsion, foam, cream, dust, gel, and lotion.

10. The composition of claim 9, wherein the second ectoparasiticide controls nymphs and/or adult ectoparasites.

11. The composition of claim 9, wherein the composition is formulated for use in a direct topical application in a form of a shampoo or lotion.

12. A composition comprising a parasiticide consisting of 5,5'-dimethyl-2,2'-dipyridyl, or a pharmaceutically, veterinary, or agriculturally acceptable salt thereof, wherein the composition is formulated for topical application and in a form selected from the group consisting of a dip, spray, aerosol, shampoo, mousse, emulsion, foam, cream, dust, gel, and lotion; and the wherein the composition includes an effective amount of 5,5'-dimethyl-2,2'-dipyridyl, or a pharmaceutically, veterinary, or agriculturally acceptable salt thereof to treat or prevent ectoparasite infestation.

13. The composition of claim 12, wherein the composition is formulated for use in a direct topical application in a form of a shampoo or lotion.

14. The composition of claim 12, wherein 5,5'-dimethyl-2,2'-dipyridyl is present at a concentration between 0.01 mM and 100 mM.

15. The composition of claim 12, wherein 5,5'-dimethyl-2,2'-dipyridyl is present at a concentration between 0.1 mM and 30 mM.

16. The composition of claim 12, wherein 5,5'-dimethyl-2,2'-dipyridyl is present at a concentration between 5 mM and 15 mM.

* * * * *